(12) United States Patent
Eissenstat et al.

(10) Patent No.: US 9,540,354 B2
(45) Date of Patent: Jan. 10, 2017

(54) DIAMIDE INHIBITORS OF CYTOCHROME P450

(71) Applicant: SEQUOIA PHARMACEUTICALS, INC., Potomac, MD (US)

(72) Inventors: Michael Eissenstat, Frederick, MD (US); Dehui Duan, Frederick, MD (US)

(73) Assignee: SEQUOIA PHARMACEUTICALS, INC., Potomac, MD (US)

( * ) Notice: Subject to any disclaimer, the term of this patent is extended or adjusted under 35 U.S.C. 154(b) by 0 days.

(21) Appl. No.: 14/565,039

(22) Filed: Dec. 9, 2014

(65) Prior Publication Data

US 2015/0087676 A1    Mar. 26, 2015

Related U.S. Application Data

(63) Continuation of application No. 12/919,008, filed as application No. PCT/US2009/034917 on Feb. 23, 2009, now Pat. No. 8,906,647.

(60) Provisional application No. 61/030,541, filed on Feb. 21, 2008.

(51) Int. Cl.

| | |
|---|---|
| *C07D 307/91* | (2006.01) |
| *C07D 405/14* | (2006.01) |
| *C07D 231/12* | (2006.01) |
| *C07D 307/79* | (2006.01) |
| *C07D 405/06* | (2006.01) |
| *C07D 405/12* | (2006.01) |
| *C07D 409/12* | (2006.01) |
| *C07D 417/12* | (2006.01) |
| *C07D 417/14* | (2006.01) |
| *A61K 31/343* | (2006.01) |
| *A61K 31/4155* | (2006.01) |
| *A61K 31/443* | (2006.01) |
| *A61K 45/06* | (2006.01) |
| *C07D 307/81* | (2006.01) |

(52) U.S. Cl.
CPC ........... *C07D 405/14* (2013.01); *A61K 31/343* (2013.01); *A61K 31/4155* (2013.01); *A61K 31/443* (2013.01); *A61K 45/06* (2013.01); *C07D 231/12* (2013.01); *C07D 307/79* (2013.01); *C07D 307/81* (2013.01); *C07D 405/06* (2013.01); *C07D 405/12* (2013.01); *C07D 409/12* (2013.01); *C07D 417/12* (2013.01); *C07D 417/14* (2013.01); *Y10T 436/14* (2015.01)

(58) Field of Classification Search
None
See application file for complete search history.

(56) References Cited

U.S. PATENT DOCUMENTS

| | | | |
|---|---|---|---|
| 8,906,647 B2 * | 12/2014 | Eissenstat | ............ C07D 231/12 435/53 |
| 2005/0267074 A1 | 12/2005 | Eissenstat et al. | |
| 2007/0004675 A1 | 1/2007 | Saavedra et al. | |

FOREIGN PATENT DOCUMENTS

| | | |
|---|---|---|
| WO | WO 03/082866 A1 | 10/2003 |
| WO | WO 2008/022345 A2 | 2/2008 |

OTHER PUBLICATIONS

Mndzhoyan, A.L; Kaldrikiyan, M. A.: Isvestiya Akademii Nauk Armyanskoi SSR , Khimicheski Nauki, vol. 15, 1962,-1962, pp. 85-94, * see the first compound in tablet on p. 90 wherein n is 3 *.

* cited by examiner

*Primary Examiner* — Satyanarayana R Gudibande
(74) *Attorney, Agent, or Firm* — Perkins Coie LLP

(57) ABSTRACT

Methods of inhibiting cytochrome P450 enzymes are provided that can be used for improving the treatment of diseases by preventing degradation of drugs or other molecules by cytochrome P450. Pharmaceutical compositions are provided that can act as boosters to improve the pharmacokinetics, enhance the bioavailability, and enhance the therapeutic effect of drugs that undergo in vivo degradation by cytochrome P450 enzymes.

22 Claims, No Drawings

DIAMIDE INHIBITORS OF CYTOCHROME P450

This application is a continuation of U.S. patent application Ser. No. 12/919,008, filed Jan. 13, 2011, which is the National Stage of International Application PCT/US2009/034917, filed Feb. 23, 2009, which claims the benefit of U.S. Provisional Application 61/030,541 filed Feb. 21, 2008, the contents of each of which are incorporated by reference in their entireties.

The technology described herein provides methods of inhibiting cytochrome P450 enzymes. The technology also provides methods of enhancing the therapeutic effect of drugs that are metabolized by cytochrome P450 enzymes, methods of decreasing the toxic effects of drugs that are metabolized to toxic by-products by cytochrome P450 enzymes, methods of increasing oral bioavailability of drugs that are metabolized by cytochrome p450 enzymes, and methods of curing diseases that are caused or exacerbated by the activity of cytochrome P450 enzymes.

BACKGROUND

Cytochrome P450 proteins (CYP(s), or alternatively P450(s)) are a family of enzymes involved in the oxidative metabolism of both endogenous and exogenous compounds. P450 enzymes are widely distributed in the liver, intestines and other tissues (Krishna et al., *Clinical Pharmacokinetics.* 26:144-160, 1994). P450 enzymes catalyze the phase I reaction of drug metabolism, to generate metabolites for excretion. The classification of P450s is based on homology of the amino acid sequence (Slaughter et al *The Annals of Pharmacotherapy* 29:619-624, 1995). In mammals, there is over 55% homology of the amino acid sequence of CYP450 subfamilies. The differences in amino acid sequence constitute the basis for a classification of the superfamily of cytochrome P450 enzymes into families, subfamilies and isozymes.

When bound to carbon monoxide (CO), the CYP proteins display a maximum absorbance (peak) at 450 nm in the visible spectra, from which its name, cytochrome P450 is derived (Omura et al., J. Biol. Chem. 239:2370, 1964). The proteins contain an iron cation and are membrane bound enzymes that can carry out electron transfer and energy transfer. Over 200 genes encoding cytochrome P450 proteins have been identified. Those genes have been divided among more than 30 gene families, which are organized into subfamilies that vary in regulation of gene expression and in amino acid sequence homology, substrate specificity, catalytic activity, and physiological role of the encoded enzymes.

Representative cytochrome P450 (CYP) genes and examples of the known substrates of CYP proteins encoded by those genes are discussed below. See also the discussion in Klassen, ed., Casarett and Doull's Toxicology: The Basic Science of Poisons, McGraw-Hill, 1996, pp. 150 ff. Further information about cytochrome P450 substrates, can be found in Gonzales and other review articles cited above. Current information sources available via the Internet include the "Cytochrome P450 Homepage", maintained by David Nelson, the "Cytochrome P450 Database", provided by the Institute of Biomedical Chemistry & Center for Molecular Design, and the "Directory of P450-containing Systems", provided by Kirill N. Degtyarenko and Peter Fabian.

CYP1A1: diethylstilbestrol, 2- and 4-hydroxyestradiol

CYP1A2: acetaminophen, phenacetin, acetanilide (analgesics), caffeine, clozapine (sedative), cyclobenzaprine (muscle relaxant), estradiol, imipramine (antidepressant), mexillitene (antiarrhythmic), naproxen (analgesic), riluzole, tacrine, theophylline (cardiac stimulant, bronchodilator, smooth muscle relaxant), warfarin.

CYP2A6: coumarin, butadiene, nicotine

CYP2A13: nicotine

CYP2B1: phenobarbital, hexobarbital

CYP2C9: NSAIDs such as diclofenac, ibuprofen, and piroxicam; oral hypoglycemic agents such as tolbutamide and glipizide; angiotensin-2 blockers such as irbesartan, losartan, and valsartan; naproxen (analgesic); phenytoin (anticonvulsant, antiepileptic); sulfamethoxazole, tamoxifen (antineoplastic); torsemide; warfarin, flurbiprofen CYP2C19: hexobarbital, mephobarbital, imipramine, clomipramine, citalopram, cycloguanil, the anti-epileptics phenytoin and diazepam, S-mephenytoin, diphenylhydantoin, lansoprazole, pantoprazole, omeprazole, pentamidine, propranolol, cyclophosphamide, progesterone CYP2D6: antidepressants (imipramine, clomipramine, desimpramine), antipsychotics (haloperidol, perphenazine, risperidone, thioridazine), beta blockers (carvedilol, S-metoprolol, propafenone, timolol), amphetamine, codeine, dextromethorphan, fluoxetine, S-mexiletine, phenacetin, propranolol CYP2E1: acetaminophen; chlorzoxazone (muscle relaxant), ethanol; caffeine, theophylline; dapsone, general anesthetics such as enflurane, halothane, and methoxyflurane; nitrosamines CYP3A4: HIV Protease Inhibitors such as indinavir, ritonavir, lopinavir, amprenavir, tipranavir, darunavir, and saquinavir; HIV integrase inhibitors such as raltegravir, Hepatitis C virus (HCV) protease inhibitors, benzodiazepines such as alprazolam, diazepam, midazolam, and triazolam; immune modulators such as cyclosporine; antihistamines such as astemizole and chlorpheniramine; HMG CoA Reductase inhibitors such as atorvastatin, cerivastatin, lovastatin, and simvastatin; channel blockers such as diltiazem, felodipine, nifedipine, nisoldipine, nitrendipine, and verapamil; antibiotics such as clarithromycin, erythromycin, and rapamycin; various steroids including cortisol, testosterone, progesterone, estradiol, ethinylestradiol, hydrocortisone, prednisone, and prednisolone; acetaminophen, aldrin, alfentanil, amiodarone, astemizole, benzphetamine, budesonide, carbamazepine, cyclophosphamide, ifosfamide, dapsone, digitoxin, quinidine (anti-arrhythmic), etoposide, flutamide, imipramine, lansoprazole, lidocaine, losartan, omeprazole, retinoic acid, FK506 (tacrolimus), tamoxifen, taxol and taxol analogs such as taxotere, teniposide, terfenadine, buspirone, haloperidol (antipsychotic), methadone, sildenafil, trazodone, theophylline, toremifene, troleandomycin, warfarin, zatosetron, zonisamide.

CYP6A1: fatty acids.

The efficacy of a drug can be dramatically affected by its metabolism in the body. In addition, the failure to maintain therapeutically effective amounts of a drug may also impact its long term efficacy. This situation may arise particularly in treatment of infectious diseases, such as viral or bacterial infections, where the inability to maintain an effective therapeutic dose can lead to the infectious agent(s) becoming drug resistant. To avoid the consequences of metabolism and sustain a therapeutically effective amount of drugs that are rapidly metabolized in a subject, or a specific tissue of a subject, the drugs often must be administered in a sustained release formulation, given more frequently and/or administered in higher dose than more slowly metabolized drugs administered by the same routes.

A common pathway of metabolism for drugs containing lipophilic moieties is via oxidation by one or more CYP enzymes. The CYP enzyme pathway metabolizes many lipophilic drugs to more polar derivatives that are more readily excreted through the kidney or liver (renal or biliary routes). That pathway renders many compounds having strong biological efficacy that would otherwise be potentially powerful therapeutics essentially useless by virtue of their rapid metabolism, which results in short half-lives in vivo, particularly where drugs are administered by the oral route.

Poor bioavailability, particularly oral bioavailability, due to first pass CYP metabolism, which leads to elimination of drugs via the liver and/or intestinal routes, is a major reason for the failure of many drug candidates in clinical trials. Where extensive metabolism by intestinal CYP occurs, first pass metabolism can lead to poor drug absorption from the GI tract. Similarly, extensive hepatic CYP metabolism can result in low circulating (plasma or blood) levels of a drug.

Alteration in drug metabolism by CYP proteins may have undesired or unexpected consequences. In some instances, metabolic by-products of CYP enzymes are highly toxic and can result in severe side effects, cancer, and even death. In other instances, alterations in CYP metabolism due to the interaction of agents may produce undesirable results.

Some examples of drug metabolism by CYP proteins and the effects of other agents on the metabolites produced by CYP proteins include:

Acetaminophen: Ethanol up-regulates CYP2E1, which metabolizes acetaminophen to a reactive quinone. This reactive quinone intermediate, when produced in sufficient amounts, causes liver damage and necrosis.

Sedatives: The sedative phenobarbital (PB) up-regulates several P450 genes, including those of the CYP2B and CYP3A subfamilies. Up regulation of these enzymes increases the metabolism and reduces the sedative effects of PB and the related sedative hexobarbital.

Antibiotics: The antibiotics rifampicin, rifampin, rifabutin, erythromycin, and related compounds are inducers of the CYP3A4 gene and are substrates of the enzyme product.

Anti-cancer agents: Taxol and taxotere are potent anti-cancer agents. Both drugs are extensively metabolized by CYP3A4 and have poor oral bioavailability. These drugs are only efficacious in parenteral formulations which, due to their poor solubility properties, are highly noxious to patients.

Nicotine: CYP2A6 and 2A13 convert nicotine, a non-toxic component of cigarette smoke, into NNK, a highly potent carcinogen that contributes to lung cancer from smoking.

Oral contraceptive/estrogen replacement therapy: Estrogens and estradiols are the active ingredients in oral contraceptives and in hormonal replacement therapies for postmenopausal women. Women who are also taking antibiotics such as rifampicin or erythromycin, or glucocorticoids such as dexamethasone, or who smoke, risk decreased efficacy of the estrogen/estradiol treatments due to increased metabolism of these compounds by up-regulated CYP3A4 and/or CYP1A2 enzymes.

Dextromethorphan: CYP2D6 metabolizes dextromethorphan to dextrorphan. Individuals who express high levels of CYP2D6 (so-called rapid metabolizers) do not receive therapeutic benefits from dextromethorphan due to extensive first-pass metabolism and rapid systemic clearance.

Protease Inhibitors: Protease inhibitors and non-nucleoside reverse transcriptase inhibitors currently indicated for use in treatment of HIV or HCV are typically good substrates of cytochrome P450 enzymes; in particular, they are metabolized by CYP3A4 enzymes (see e.g., Sahai, AIDS 10 Suppl 1:S21-5, 1996) with possible participation by CYP2D6 enzymes (Kumar et al., *J. Pharmacol. Exp. Ther.* 277(1):423-31, 1996). Although protease inhibitors are reported to be inhibitors of CYP3A4, some non-nucleoside reverse transcriptase inhibitors, such as nevirapine and efavirenz, are inducers of CYP3A4 (see e.g. Murphy et al., *Expert Opin. Invest. Drugs* 5/9: 1183-99, 1996).

Human CYP isozymes are widely distributed among tissues and organs (Zhang et al., *Drug Metabolism and Disposition.* 27:804-809, 1999). With the exception of CYP1A1 and CYP2A13, most human CYP isozymes are located in the liver, but are expressed at different levels (Waziers J. Pharmacol. Exp. Ther. 253: 387, 1990). A solution to the problem of drug degradation and first-pass metabolism is to control the rate of drug metabolism. When the rates of drug absorption and metabolism reach a steady state, a maintenance dose can be delivered to achieve a desired drug concentration that is required for drug efficacy. Certain natural products have been shown to increase bioavailability of a drug. For example, the effect of grapefruit juice on drug pharmacokinetics is well known. See Edgar et al., Eur. J. Clin. Pharmacol. 42:313, (1992); Lee et al., Clin. Pharmacol. Ther. 59:62, (1996); Kane et al., Mayo Clinic Proc. 75:933, (2000). This effect of grapefruit juice is due to the presence of natural P450-inhibiting components. Other compounds also have been used for inhibition of P450. For example, the HIV-1 protease inhibitor Ritonavir® is now more commonly prescribed for use in combination with other, more effective HIV protease inhibitors because of its ability to "boost" those other compounds by inhibiting P450-mediated degradation.

Present methods of inhibiting cytochrome P450 enzymes are not wholly satisfactory because of toxicity issues, high cost, and other factors. For example, using ritonavir to inhibit cytochrome P450 is not desirable in disorders other than HIV infection. It is apparent, therefore, that new and improved methods of inhibiting cytochrome P450 enzymes are greatly to be desired. In particular, methods where an inhibitor can be co-administered with another biologically active compound (e.g., a drug) that is metabolized by cytochrome P450 enzymes are highly desirable.

SUMMARY

The technology described herein provides, among other things, methods and compounds for inhibiting cytochrome P450 enzymes. The technology also provides methods of enhancing the therapeutic effect of drugs that are metabolized by cytochrome P450 enzymes, methods of decreasing the toxic effects of drugs that are metabolized to toxic by-products by cytochrome P450 enzymes, methods of increasing oral bioavailability of drugs that are metabolized by cytochrome P450 enzymes, and methods of curing diseases that are caused or exacerbated by the activity of cytochrome P450 enzymes.

An advantage of the technology described herein is that it provides improved inhibitors of cytochrome P450 enzymes. Another advantage is that it provides a method of controlling the pharmacokinetic properties of drugs. Another advantage is that it helps control the rate of metabolism of drugs. Another advantage is that it controls the degradation of drugs. Another advantage is that it enhances the bioavailability of drugs. Another advantage is that it enhances the efficacy of drugs. Another advantage is that it boosts the efficacy of certain drugs so that the drugs can be administered at a lower concentration or dosage thereby reducing their toxicity. Another advantage is that these properties can lower the overall cost associated with the treatment of disorders.

In one aspect, the technology described herein provides both compounds of formula (I), and a method of inhibiting a cytochrome P450 monooxygenase enzyme by contacting it with a compound of formula (I) having the structure:

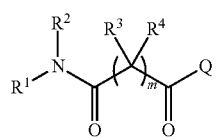

(I)

wherein:
Q is —NR$^5$R$^6$ or Q is —OR$^5$ and R$^6$ is absent;
m is 1-3;
at least one of the R$^1$, R$^2$, R$^3$, R$^4$, R$^5$, and R$^6$ groups present is C$_1$-C$_6$ alkyl substituted with an optionally substituted benzofuran;
each of R$^1$, R$^2$, R$^3$, R$^4$, R$^5$, and R$^6$ that is present is independently is selected from the group consisting of H, optionally substituted C$_1$-C$_8$ alkyl, optionally substituted C$_3$-C$_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl;
where each optional substituent is independently selected from the group consisting of halo, —CN, —NO$_2$, —CO$_n$R, —CON(R)$_2$, —C(S)R, —C(S)N(R)$_2$, —SO$_n$N(R)$_2$, —SR, —SO$_n$R, —N(R)$_2$, —N(R)CO$_n$R, —NRS(O)$_n$R, —NRC[=N(R)]N(R)$_2$, —N(R)N(R)CO$_n$R, —NRPO$_n$N(R)$_2$, —NRPO$_n$OR, oxo, =N—OR, =N—N(R)$_2$, =NR, =NNRC(O)N(R)$_2$, =NNRCO$_n$R, =NNRS(O)$_n$N(R)$_2$, =NNRS(O)$_n$(R) C$_1$-C$_8$ alkyl, —OR, alkyl, C$_2$-C$_6$ alkenyl, C$_2$-C$_6$ alkynyl, C$_3$-C$_8$ cycloalkyl, C$_5$-C$_8$ cycloalkenyl, heterocyclo, aryl, and heteroaryl;
each R is independently selected from the group consisting of: H, C$_1$-C$_8$ alkyl, C$_3$-C$_8$ cycloalkyl, cycloalkylalkyl, aryl, aralkyl, heteroaryl, heteroaralkyl, heterocyclo, heterocycloalkyl, and heterocycloalkylalkyl; and
each n is independently 1 or 2;
provided that at least two of the R$^1$, R$^2$, R$^3$, R$^4$, R$^5$, and R$^6$ groups present are not H; and
provided that when Q is —NR$^5$R$^6$, R$^1$ and R$^2$ are isobutyl, R$^3$ and R$^4$ are H, and R$^5$ is —CH$_2$-[5]-benzofuranyl, then R$^6$ cannot be —CH$_2$-4-pyridyl, —CH$_2$-1,5-dimethyl-3-pyrazole, or —CH2-4-methyl-2-thiazole.

In one embodiment compounds of formula (I) are compounds of formula (II), in which Q is —NR$^5$R$^6$, and the compounds have the structure:

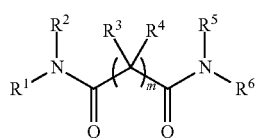

(II)

wherein:
m is 1-3;
at least one of R$^1$, R$^2$, R$^3$, R$^4$, R$^5$, and R$^6$ is C$_1$-C$_6$ alkyl substituted with an optionally substituted benzofuran;
each R$^1$, R$^2$, R$^3$, R$^4$, R$^5$, and R$^6$ independently is selected from the group consisting of H, optionally substituted C$_1$-C$_8$ alkyl, optionally substituted C$_3$-C$_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl;
where each optional substituent is independently selected from the group consisting of halo, —CN, —NO$_2$, —CO$_n$R, —CON(R)$_2$, —C(S)R, —C(S)N(R)$_2$, —SO$_n$N(R)$_2$, —SR, —SO$_n$R, —N(R)$_2$, —N(R)CO$_n$R, —NRS(O)$_n$R, —NRC[=N(R)]N(R)$_2$, —N(R)N(R) CO$_n$R, —NRPO$_n$N(R)$_2$, —NRPO$_n$OR, oxo, =N—OR, =N—N(R)$_2$, =NR, =NNRC(O)N(R)$_2$, =NNRCO$_n$R, =NNRS(O)$_n$N(R)$_2$, =NNRS(O)$_n$(R) C$_1$-C$_8$ alkyl, OR, C$_1$-C$_8$ alkyl, C$_2$-C$_6$ alkenyl, C$_2$-C$_6$ alkynyl, C$_3$-C$_8$ cycloalkyl, C$_5$-C$_8$ cycloalkenyl, heterocyclo, aryl, and heteroaryl;
each R is independently selected from the group consisting of: H, C$_1$-C$_8$ alkyl, C$_3$-C$_8$ cycloalkyl, cycloalkylalkyl, aryl, aralkyl, heteroaryl, heteroaralkyl, heterocyclo, heterocycloalkyl, and heterocycloalkylalkyl; and
each n is independently 1 or 2;
or a stereoisomeric form or pharmacologically acceptable salt thereof;
provided that at least two of R$^1$, R$^2$, R$^3$, R$^4$, R$^5$, and R$^6$ are not H; and
provided that when R$^1$ and R$^2$ are isobutyl, R$^3$ and R$^4$ are H, and R$^5$ is CH$_2$-[5]-benzofuranyl, then R$^6$ cannot be —CH$_2$-4-pyridyl, —CH$_2$-1,5-dimethyl-3-pyrazolyl, or —CH2-4-methyl-2-thiazolyl.

In another embodiment, the compounds of formula (I) are compounds of formula (III) in which Q is —OR$^5$, and the compounds have the structure:

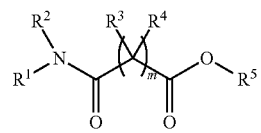

(III)

wherein:
m is 1-3;
at least one of R$^1$, R$^2$, R$^3$, R$^4$, and R$^5$ is C$_1$-C$_6$ alkyl substituted with an optionally substituted benzofuran;
each R$^1$, R$^2$, R$^3$, R$^4$, and R$^5$ independently is selected from the group consisting of H, optionally substituted C$_1$-C$_8$ alkyl, optionally substituted C$_3$-C$_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl;
where each optional substituent is independently selected from the group consisting of halo, —CN, —NO$_2$, —CO$_n$R, —CON(R)$_2$, —C(S)R, —C(S)N(R)$_2$, —SO$_n$N(R)$_2$, —SR, —SO$_n$R, —N(R)$_2$, —N(R)CO$_n$R, —NRS(O)$_n$R, —NRC[=N(R)]N(R)$_2$, —N(R)N(R)

CO$_n$R, —NRPO$_n$N(R)$_2$, —NRPO$_n$OR, oxo, =N—OR, =N—N(R)$_2$, =NR, =NNRC(O)N(R)$_2$, =NNRCO$_n$R, =NNRS(O)$_n$N(R)$_2$, =NNRS(O)$_n$(R) C$_1$-C$_8$ alkyl, OR, C$_1$-C$_8$ alkyl, C$_2$-C$_6$ alkenyl, C$_2$-C$_6$ alkynyl, C$_3$-C$_8$ cycloalkyl, C$_5$-C$_8$ cycloalkenyl, heterocyclo, aryl, and heteroaryl;

each R is independently selected from the group consisting of: H, C$_1$-C$_8$ alkyl, C$_3$-C$_8$ cycloalkyl, cycloalkylalkyl, aryl, aralkyl, heteroaryl, heteroaralkyl, heterocyclo, heterocycloalkyl, and heterocycloalkylalkyl; and each n is independently 1 or 2;

or a stereoisomeric form or pharmacologically acceptable salt thereof;

provided that at least two of R$^1$, R$^2$, R$^3$, R$^4$, and R$^5$ are not H.

In another aspect, the technology provides a pharmaceutical composition comprising a pharmaceutically acceptable diluent, carrier, or excipient and a compound of formula (I), or a compound of any subgrouping thereof, including, but not limited to, a compound of formula (II), a compound of formula (III), and a compound selected from the compounds in Table 1.

In another aspect, the technology provides a method of inhibiting cytochrome P450 monooxygenase activity in a subject, comprising administering to the subject an effective amount of a compound according to formula (I) or a pharmaceutical composition comprising a compound of formula (I). In some embodiments the compound may be a compound of formula (II), a compound of formula (III), or a compound set forth in Table 1.

In yet another aspect, the technology provides a method of reducing toxicity in a subject of a compound that is metabolized by a cytochrome P450 monooxygenase to a toxic metabolite, the method comprising administering to the subject an effective amount of a compound according to formula (I), formula (II), formula (III), or a compound set forth in Table 1.

In some embodiments, where a compound of formula (I), formula (II), formula (III), or a compound set forth in Table 1, is administered with a drug whose efficacy is compromised due to degradation by cytochrome P450, the compound is administered prior to, and/or substantially contemporaneously with, the drug. In other embodiments, the compound can be administered at least 30 minutes, at least 1 hour, at least 2 hours, or at least 12 hours prior to administration of the drug. In other embodiments the compound is co-administered with the drug, in either the same dosage (e.g., combined) or in separate dosages (e.g., two different tablets).

In yet another aspect, the technology provides a composition comprising a compound of formula (I), formula (II), or formula (III), where the composition further comprises an effective amount of a drug where efficacy of the drug is compromised due to degradation by cytochrome P450 monooxygenase. The drug may be, for example, Cyclosporine, Tacrolimus (FK506), Sirolimus (rapamycin), Indinavir, Ritonavir, Saquinavir, Felodipine, Isradipine, Nicardipine, Nisoldipine, Nimodipine, Nitrendipine, Nifedipine, Verapamil, Etoposide, Tamoxifen, Vinblastine, Vincristine, Taxol, Atorvastatin, Fluvastatin, Lovastatin, Pravastatin, Simvastatin, Terfenadine, Loratadine, Astemizole, Alfentanil, Carbamazepine, Azithromycin, Clarithromycin, Erythromycin, Itraconazole, Rifabutin, Lidocaine, Cisapride, Sertraline, Pimozide, Triazolam, Anastrazole, Busulfan, Corticosteroids (dexamethasone, methylprednisone and prednisone), Cyclophosphamide, Cytarabine, Docetaxel, Doxorubicin, Erlotinib, Exemestane, Gefitinib, Idarubicin, Ifosphamide, Imatinib mesylate, Irinotecan, Ketoconazole, Letrozole, Paclitaxel, Teniposide, Tretinoin, Vinorelbine, quinidine; alprazolam, diazepam, midazolam, nelfinavir, chlorpheniramine, amlodipine, diltiazem, lercanidipine, cerivastatin, estradiol, hydrocortisone, progesterone, testosterone, alfentanyl, aripiprazole, cafergot, caffeine, cilostazol, cocaine, codeine, dapsone, dextromethorphan, domperidone, eplerenone, fentanyl, finasteride, gleevec, haloperidol, irinotecan, Levo-Alpha Acetyl Methadol (LAAM), methadone, nateglinide, odanestron, propranolol, quinine, salmeterol, sildenafil, trazodone, vincristine, zaleplon, zolpidem, ixabepilone, Agenerase (APV), Aptivus (TPV), Crixivan (IDV), Invirase (SQV), Lexiva (FPV), Prezista (DRV), Reyataz (ATV) Viracept (NFV), Elvitegravir, Selzentry, Vicriviroc, Telaprevir, Telithromycin, tandospirone or buspirone.

Each of the aspects and embodiments of the technology discussed above can include one or more of the following embodiments of compound of formula (I), formula (II), or formula (III).

In some embodiments, for example when m is 1, R$^5$ is C$_1$-C$_6$ alkyl substituted with an otherwise unsubstituted benzofuran, wherein said alkyl is linked to the 4, 5, 6, or 7 position of the benzofuran, e.g. R$^5$ is —CH$_2$-5-benzofuran:

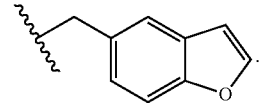

In other embodiments, R$^3$ is H and R$^4$ is selected from the group consisting of H, optionally substituted C$_1$-C$_8$ alkyl, optionally substituted C$_3$-C$_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl. In such an embodiment R$^5$ may be C$_1$-C$_6$ alkyl substituted with an otherwise unsubstituted benzofuran, wherein said alkyl is linked to the 4, 5, 6, or 7 position of the benzofuran, e.g. R$^5$ is —CH$_2$-5-benzofuran

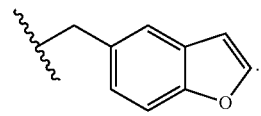 [SMILES: *Cc1ccc2occc2c1]

In some embodiments R$^1$ is optionally substituted C$_1$-C$_8$ alkyl.

In some embodiments R$^2$ is optionally substituted C$_1$-C$_8$ alkyl.

In some embodiments R$^4$ is optionally substituted alkyl or optionally substituted heteroaralkyl.

In some embodiments where Q is —NR$^5$R$^6$, R$^6$ is H, optionally substituted C$_1$-C$_8$ alkyl, or optionally substituted heteroaralkyl.

In some embodiments R$^1$ and R$^2$ are optionally substituted C$_1$-C$_8$ alkyl.

In some embodiments where Q is —NR$^5$R$^6$, R$^3$ is H, R$^4$ is H, optionally substituted C$_1$-C$_8$ alkyl or optionally substituted heteroaralkyl, and R$^6$ is H, optionally substituted C$_1$-C$_8$ alkyl or optionally substituted heteroaralkyl.

In some embodiments $R^3$ is

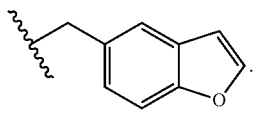 [SMILES: *Cc1ccc2occc2c1]

In some embodiments $R^4$ is H or $C_1$-$C_8$ alkyl.

In some embodiments $R^4$ is H.

In some embodiments, for example where Q is —$NR^5R^6$, $R^4$ is H and $R^5$ is H.

In some embodiments $R^6$ is selected from the group consisting of optionally substituted $C_1$-$C_8$ alkyl, optionally substituted $C_3$-$C_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl.

In some embodiments $R^1$ is $C_1$-$C_6$ alkyl substituted with an otherwise unsubstituted benzofuran, wherein said alkyl is linked to the 4, 5, 6, or 7 position of the benzofuran, for example, when m is 1,

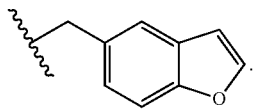 [SMILES: *Cc1ccc2occc2c1]

In some embodiments $R^3$ and $R^4$ are each independently heteroaralkyl.

In some embodiments $R^3$ and $R^4$ are each independently heteroaryl methyl.

In some embodiments the compounds are selected from the compounds listed in Table 1.

In some embodiments the cytochrome P450 monooxygenase is CYP3A4 or CYP3A5.

In some embodiments, for example when Q is —$OR^5$, $R^5$ is not H. In other embodiments, where Q is —$OR^5$, $R^5$ is $C_1$-$C_6$ alkyl substituted with benzofuran, e.g.,

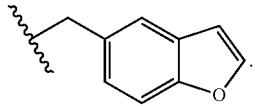 [SMILES: *Cc1ccc2occc2c1]

In some embodiments, the technology described herein provides for a compound of formula (I), (II) or (III), wherein at least three of the $R^1$, $R^2$, $R^3$, $R^4$, $R^5$, and $R^6$ groups present are not H. The technology also provides for pharmaceutical compositions comprising such compounds, method of inhibiting cytochrome P450 monooxygenase in a subject with such compounds, and methods wherein such compounds are administered with a drug whose efficacy is compromised due to degradation by cytochrome P450.

In other embodiments, for example where Q is —$NR^5R^6$, neither $R^5$ nor $R^6$ are H.

In some embodiments, where a compound of formula (I), formula (II), formula (III), or one of the above-mentioned embodiments thereof, is administered to a subject, the subject is a patient is suffering from chronic pain, depression, epilepsy, psychosis, inflammation, cancer, cardiovascular disease, diabetes, neurodegenerative disease, and/or infection. In other embodiments the patient is suffering from HCV or HIV infection.

The details of one or more examples are set forth in the accompanying reaction schemes and description. Further features, aspects, and advantages of the technology will become apparent from the description, the schemes, and the claims.

DETAILED DESCRIPTION

The technology described herein provides compounds and methods of inhibiting cytochrome P450 (CYP) enzymes. More particularly, the technology provides methods for enhancing the therapeutic effect of drugs in which the efficacy is compromised due to degradation mediated by cytochrome P450. The methods include administering compounds or pharmaceutical compositions containing the compounds in any therapeutic regimen where one or more primary drugs are metabolized by a CYP. The compounds or pharmaceutical compositions can be administered when the primary drug either becomes inactive or is converted to a toxic metabolite due to metabolism by a CYP. The compounds or compositions can inhibit or reduce the rate of degradation of drugs that are effective against a variety of diseases and that are degraded by one or more cytochrome P450 enzymes. Upon co-administration, the compounds and compositions can, for example, maintain intracellular concentrations of the drugs at a therapeutic level for a sustained period of time. The methods are useful, for example, in treating a variety of disorders such as, cardiac arrhythmia, depression, psychosis, chronic pain, and infections such as HIV or HCV. The compounds or compositions can be administered either alone or in combination with drugs such as analgesics, anti-depressants, anti-psychotics, antibiotics, anti-arrhythmics, steroids, anesthetics, muscle relaxants, cardiac stimulants, NSAIDs, anti-epileptics, or protease inhibitors, such as HIV or HCV protease inhibitors.

More particularly, in one aspect, the technology described herein provides compounds of formula (I), its stereoisomeric forms, and pharmacologically acceptable salts of compounds of formula (I) or its individual stereochemical forms. The technology described herein also provides methods of inhibiting a cytochrome P450 monooxygenase enzyme by contacting it with a compound of formula (I):

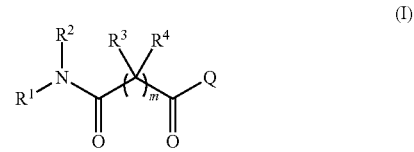

wherein:
Q is —$NR^5R^6$ or Q is —$OR^5$ and $R^6$ is absent;
m is 1-3;
at least one of the $R^1$, $R^2$, $R^3$, $R^4$, $R^5$, and $R^6$ groups present is $C_1$-$C_6$ alkyl substituted with an optionally substituted benzofuran;
each of $R^1$, $R^2$, $R^3$, $R^4$, $R^5$, and $R^6$ that is present is independently is selected from the group consisting of H, optionally substituted $C_1$-$C_8$ alkyl, optionally substituted $C_3$-$C_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl;

where each optional substituent is independently selected from the group consisting of halo, —CN, —NO$_2$, —CO$_n$R, —CON(R)$_2$, —C(S)R, —C(S)N(R)$_2$, —SO$_n$N(R)$_2$, —SR, —SO$_n$R, —N(R)$_2$, —N(R)CO$_n$R, —NRS(O)$_n$R, —NRC[=N(R)]N(R)$_2$, —N(R)N(R)CO$_n$R, —NRPO$_n$N(R)$_2$, —NRPO$_n$OR, oxo, =N—OR, =N—N(R)$_2$, =NR, =NNRC(O)N(R)$_2$, =NNRCO$_n$R, =NNRS(O)$_n$N(R)$_2$, =NNRS(O)$_n$(R) C$_1$-C$_8$ alkyl, —OR, alkyl, C$_2$-C$_6$ alkenyl, C$_2$-C$_6$ alkynyl, C$_3$-C$_8$ cycloalkyl, C$_5$-C$_8$ cycloalkenyl, heterocyclo, aryl, and heteroaryl;

each R is independently selected from the group consisting of: H, C$_1$-C$_8$ alkyl, C$_3$-C$_8$ cycloalkyl, cycloalkylalkyl, aryl, aralkyl, heteroaryl, heteroaralkyl, heterocyclo, heterocycloalkyl, and heterocycloalkylalkyl; and each n is independently 1 or 2;

provided that at least two of the $R^1$, $R^2$, $R^3$, $R^4$, $R^5$, and $R^6$ groups present are not H; and provided that when Q is —NR$^5$R$^6$, $R^1$ and $R^2$ are isobutyl, $R^3$ and $R^4$ are H, and $R^5$ is —CH$_2$[5]-benzofuranyl, then $R^6$ cannot be —CH$_2$-4-pyridyl, —CH$_2$-1,5-dimethyl-3-pyrazole, or —CH2-4-methyl-2-thiazole.

In one embodiment compounds of formula (I) are compounds of formula (II), in which Q is —NR$^5$R$^6$, and the compounds have the structure:

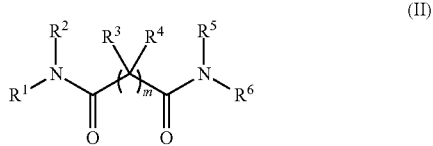

(II)

wherein:
m is 1-3;
at least one of $R^1$, $R^2$, $R^3$, $R^4$, $R^5$, and $R^6$ is C$_1$-C$_6$ alkyl substituted with an optionally substituted benzofuran;
each $R^1$, $R^2$, $R^3$, $R^4$, $R^5$, and $R^6$ independently is selected from the group consisting of H, optionally substituted C$_1$-C$_8$ alkyl, optionally substituted C$_3$-C$_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl;
where each optional substituent is independently selected from the group consisting of halo, —CN, —NO$_2$, —CO$_n$R, —CON(R)$_2$, —C(S)R, —C(S)N(R)$_2$, —SO$_n$N(R)$_2$, —SR, —SO$_n$R, —N(R)$_2$, —N(R)CO$_n$R, —NRS(O)$_n$R, —NRC[=N(R)]N(R)$_2$, —N(R)N(R)CO$_n$R, —NRPO$_n$N(R)$_2$, —NRPO$_n$OR, oxo, =N—OR, =N—N(R)$_2$, =NR, =NNRC(O)N(R)$_2$, =NNRCO$_n$R, =NNRS(O)$_n$N(R)$_2$, =NNRS(O)$_n$(R) C$_1$-C$_8$ alkyl, OR, C$_1$-C$_8$ alkyl, C$_2$-C$_6$ alkenyl, C$_2$-C$_6$ alkynyl, C$_3$-C$_8$ cycloalkyl, C$_5$-C$_8$ cycloalkenyl, heterocyclo, aryl, and heteroaryl;
each R is independently selected from the group consisting of: H, C$_1$-C$_8$ alkyl, C$_3$-C$_8$ cycloalkyl, cycloalkylalkyl, aryl, aralkyl, heteroaryl, heteroaralkyl, heterocyclo, heterocycloalkyl, and heterocycloalkylalkyl; and
each n is independently 1 or 2;

or a stereoisomeric form or pharmacologically acceptable salt thereof;
provided that at least two of $R^1$, $R^2$, $R^3$, $R^4$, $R^5$, and $R^6$ are not H; and
provided that when $R^1$ and $R^2$ are isobutyl, $R^3$ and $R^4$ are H, and $R^5$ is CH$_2$-[5]-benzofuranyl, then $R^6$ cannot be —CH$_2$-4-pyridyl, —CH$_2$-1,5-dimethyl-3-pyrazolyl, or —CH2-4-methyl-2-thiazolyl.

In another embodiment, the compounds of formula (I) are compounds of formula (III), in which Q is —OR$^5$, and the compounds have the structure:

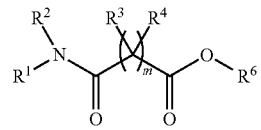

(III)

wherein:
m is 1-3;
at least one of $R^1$, $R^2$, $R^3$, $R^4$, and $R^5$ is C$_1$-C$_6$ alkyl substituted with an optionally substituted benzofuran;
each $R^1$, $R^2$, $R^3$, $R^4$, and $R^5$ independently is selected from the group consisting of H, optionally substituted C$_1$-C$_8$ alkyl, optionally substituted C$_3$-C$_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl;
where each optional substituent is independently selected from the group consisting of halo, —CN, —NO$_2$, —CO$_n$R, —CON(R)$_2$, —C(S)R, —C(S)N(R)$_2$, —SO$_n$N(R)$_2$, —SR, —SO$_n$R, —N(R)$_2$, —N(R)CO$_n$R, —NRS(O)$_n$R, —NRC[=N(R)]N(R)$_2$, —N(R)N(R)CO$_n$R, —NRPO$_n$N(R)$_2$, —NRPO$_n$OR, oxo, =N—OR, =N—N(R)$_2$, =NR, =NNRC(O)N(R)$_2$, =NNRCO$_n$R, =NNRS(O)$_n$N(R)$_2$, =NNRS(O)$_n$(R) C$_1$-C$_8$ alkyl, OR, C$_1$-C$_8$ alkyl, C$_2$-C$_6$ alkenyl, C$_2$-C$_6$ alkynyl, C$_3$-C$_8$ cycloalkyl, C$_5$-C$_8$ cycloalkenyl, heterocyclo, aryl, and heteroaryl;
each R is independently selected from the group consisting of: H, C$_1$-C$_8$ alkyl, C$_3$-C$_8$ cycloalkyl, cycloalkylalkyl, aryl, aralkyl, heteroaryl, heteroaralkyl, heterocyclo, heterocycloalkyl, and heterocycloalkylalkyl; and
each n is independently 1 or 2;
or a stereoisomeric form or pharmacologically acceptable salt thereof;
provided that at least two of $R^1$, $R^2$, $R^3$, $R^4$, and $R^5$ are not H.

In another aspect, the technology provides a pharmaceutical composition including a compound according to formula (I), (II), or (III) and a pharmaceutically acceptable diluent, carrier, or excipient.

In yet another aspect, the technology provides a method of inhibiting cytochrome P450 monooxygenase in a subject, comprising administering to the subject an effective amount of a compound according to formula (I), (II), or (III). In some embodiments the cytochrome P450 monooxygenase is CYP3A4 or CYP3A5.

In another aspect, the technology provides a method of reducing toxicity in a subject of a compound that is metabolized by cytochrome P450 monooxygenase to a toxic metabolite, comprising administering to the subject an effective amount of a compound according to formula (I), (II), or (III) to inhibit the cytochrome P450 monooxygenase. In some embodiments the cytochrome P450 monooxygenase that metabolizes the compound is CYP3A4 or CYP3A5.

In yet another aspect, the technology provides a composition comprising a compound of formula (I), (II), or (III), and further comprising an effective amount of a drug where the efficacy of the drug is compromised due to degradation by cytochrome P450 monooxygenase. In some embodiments the cytochrome P450 monooxygenase is CYP3A4 or CYP3A5.

Each of the aspects and embodiments of the technology discussed above can include one or more of the following embodiments, including the following embodiments of a compound of formula (I), formula (II), or formula (III).

In some embodiments $R^5$ is $C_1$-$C_6$ alkyl substituted with an otherwise unsubstituted benzofuran, wherein said alkyl is linked to the 4, 5, 6 or 7 position of the benzofuran, for example, when m is 1,

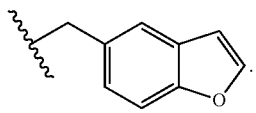 [SMILES: *Cc1ccc2occc2c1]

In other embodiments, $R^3$ is H and $R^4$ is selected from the group consisting of H, optionally substituted $C_1$-$C_8$ alkyl, optionally substituted $C_3$-$C_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl. In such an embodiment $R^5$ may be $C_1$-$C_6$ alkyl substituted with an otherwise unsubstituted benzofuran, wherein said alkyl is linked to the 4, 5, 6 or 7 position of the benzofuran, e.g. $R^5$ is —$CH_2$-5-benzofuran

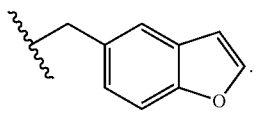 [SMILES: *Cc1ccc2occc2c1]

In some embodiments $R^1$ is optionally substituted $C_1$-$C_8$ alkyl.

In some embodiments $R^2$ is optionally substituted $C_1$-$C_8$ alkyl.

In some embodiments $R^4$ is optionally substituted alkyl or optionally substituted heteroaralkyl.

In some embodiments, where Q is —$NR^5R^6$, $R^6$ is H, optionally substituted $C_1$-$C_8$ alkyl, or optionally substituted heteroaralkyl.

In some embodiments $R^1$ and $R^2$ are optionally substituted $C_1$-$C_8$ alkyl.

In some embodiments where Q is —$NR^5R^6$, $R^3$ is H, $R^4$ is H, optionally substituted $C_1$-$C_8$ alkyl or optionally substituted heteroaralkyl, and $R^6$ is H, optionally substituted $C_1$-$C_8$ alkyl or optionally substituted heteroaralkyl.

In some embodiments $R^3$ is $C_1$-$C_6$ alkyl substituted with an otherwise unsubstituted benzofuran, wherein said alkyl is linked to the 4, 5, 6, or 7 position of the benzofuran. For example, when m is 1, $R^3$ is

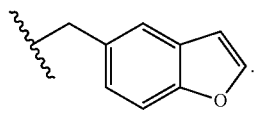

In other embodiments $R^3$ is

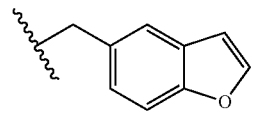 [SMILES: *Cc1ccc2occc2c1]

regardless of the value of m.

In some embodiments $R^4$ is H or $C_1$-$C_8$ alkyl.
In some embodiments $R^4$ is H.
In some embodiments, for example where Q is —$NR^5R^6$, $R^4$ is H and $R^5$ is H.

In some embodiments $R^6$ is selected from the group consisting of optionally substituted $C_1$-$C_8$ alkyl, optionally substituted $C_3$-$C_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl.

In some embodiments $R^1$ is $C_1$-$C_6$ alkyl substituted with an otherwise unsubstituted benzofuran, wherein said alkyl is linked to the 4, 5, 6, or 7 position of the benzofuran, for example, when m is 1,

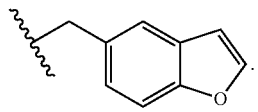

In some embodiments $R^3$ and $R^4$ are each independently heteroaralkyl.

In some embodiments $R^3$ and $R^4$ are each independently heteroaryl methyl.

In some embodiments the compounds are selected from the compounds listed in Table 1.

In some embodiments the cytochrome P450 monooxygenase is CYP3A4 or CYP3A5.

In some embodiments, for example when Q is —$OR^5$, $R^5$ is not H. In other embodiments, where Q is —$OR^5$, $R^5$ is $C_1$-$C_6$ alkyl substituted with benzofuran, e.g.,

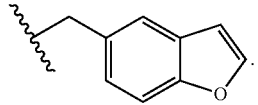

In other embodiments, for example where Q is —$NR^5R^6$, neither $R^5$ nor $R^6$ are H.

In some embodiments, compounds formula I and compositions comprising compounds of formula I are limited to those comprising compounds of the formula (II) or compounds of formula (III), wherein the $R^1$, $R^2$, $R^3$, $R^4$, $R^5$ and $R^6$ group present in the compounds are independently selected from those found in the following table.

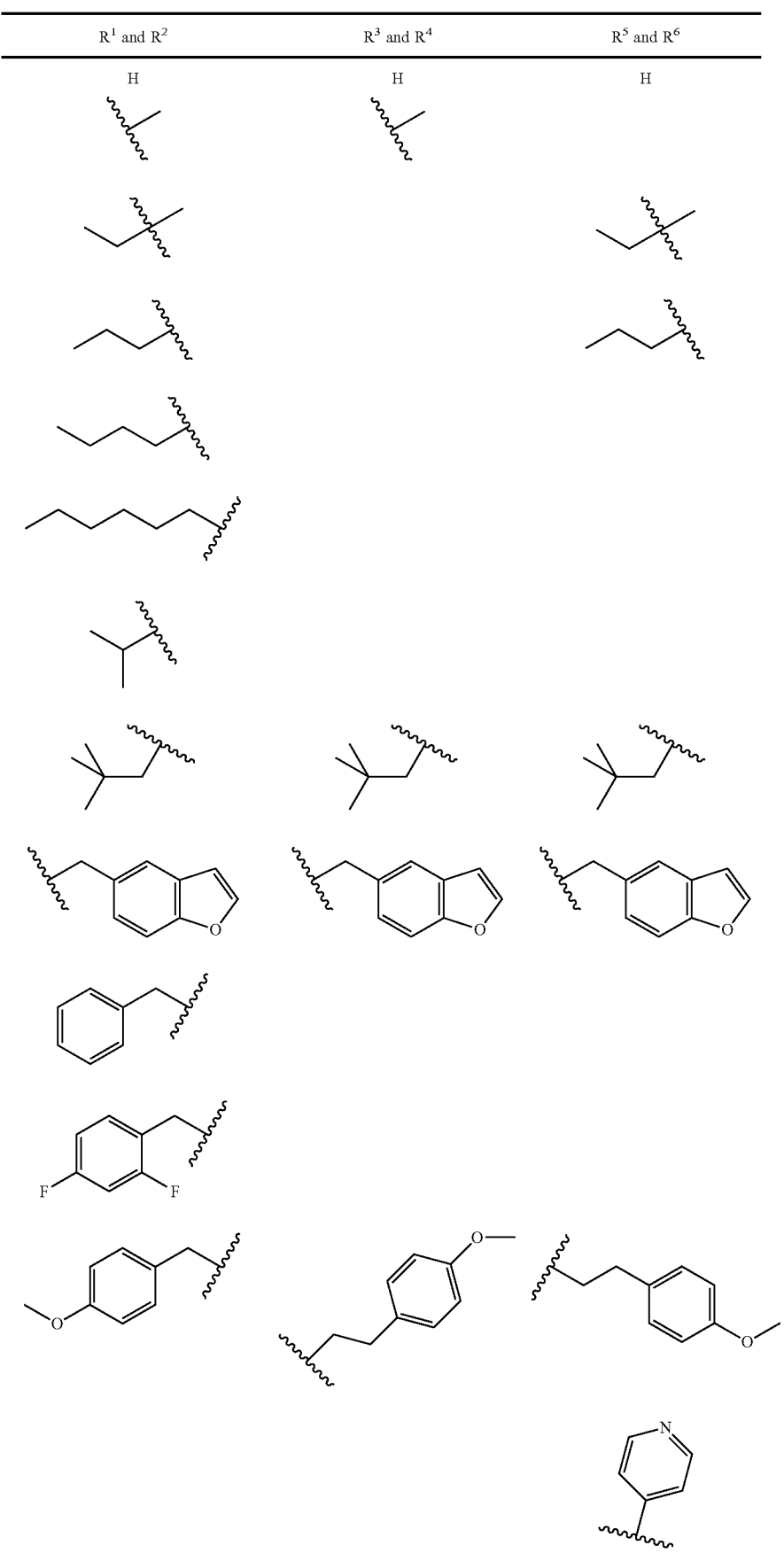

-continued
| R¹ and R² | R³ and R⁴ | R⁵ and R⁶ |
|---|---|---|
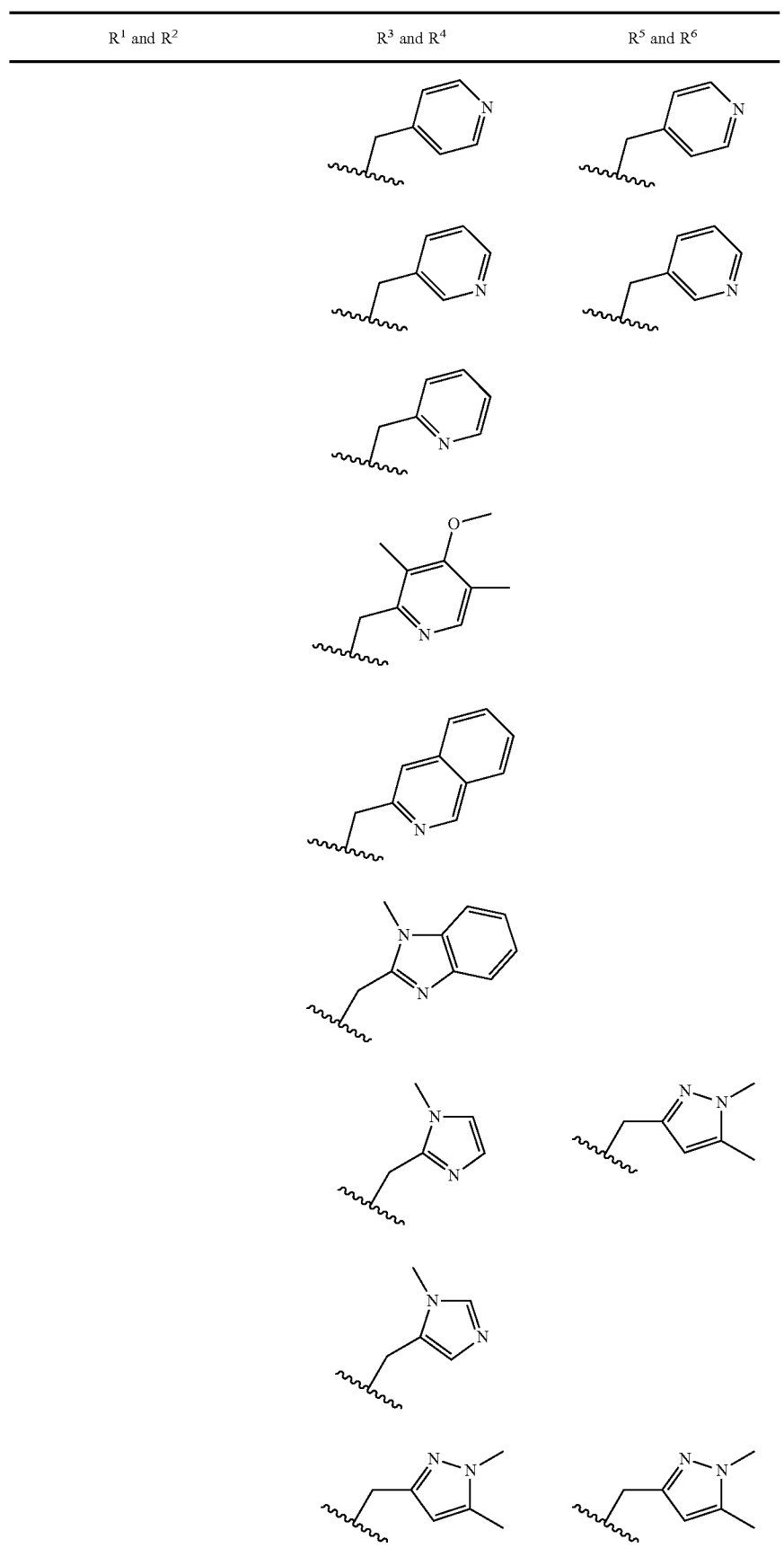

| R¹ and R² | R³ and R⁴ | R⁵ and R⁶ |
|---|---|---|
| | 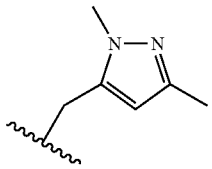 [SMILES: *Cc1cc(C)nn1C] | |
| | 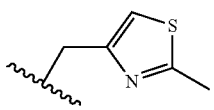 [SMILES: *Cc1csc(C)n1] | |
| | 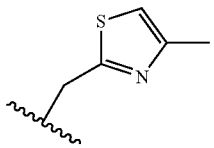 [SMILES: *Cc1nc(C)cs1] | |
| | 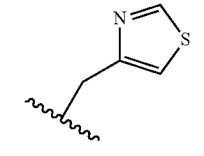 [SMILES: *Cc1cscn1] | |
| | 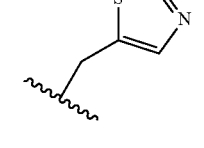 | |
| | 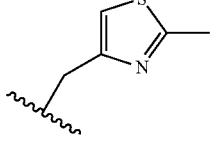 | |
| 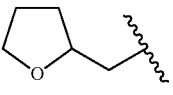 [SMILES: *CC1CCCO1] | | 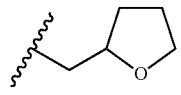 [SMILES: *CC1CCCO1] |

In some embodiments the compounds of formula (I) are selected from the compounds listed in Table 1. It will be recognized that the compounds in Table 1 are merely illustrative examples and are not limiting. All compounds in Table I have an $IC_{50}$ less than 100 nM for the metabolism of dibenzylfluorescein (DBF) by human liver microsomes (Xeno Tech, LLC, Lenexa, Kans.). Where tested, the compounds also have an $IC_{50}$ less than 100 nM for the inhibition of DBF metabolism by CYP 3A4 bactosomes.

TABLE 1

Cmpd. 1

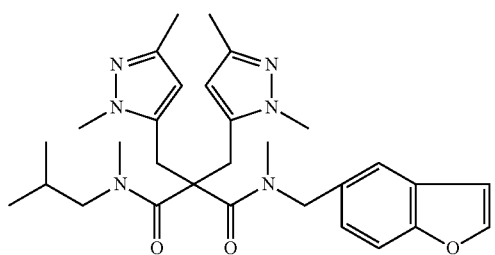 [SMILES: Cc1cc(CC(Cc2cc(C)nn2C)(C(=O)N(C)Cc2ccc3occc3c2)C(=O)N(C)CC(C)C)n(C)n1]

TABLE 1-continued
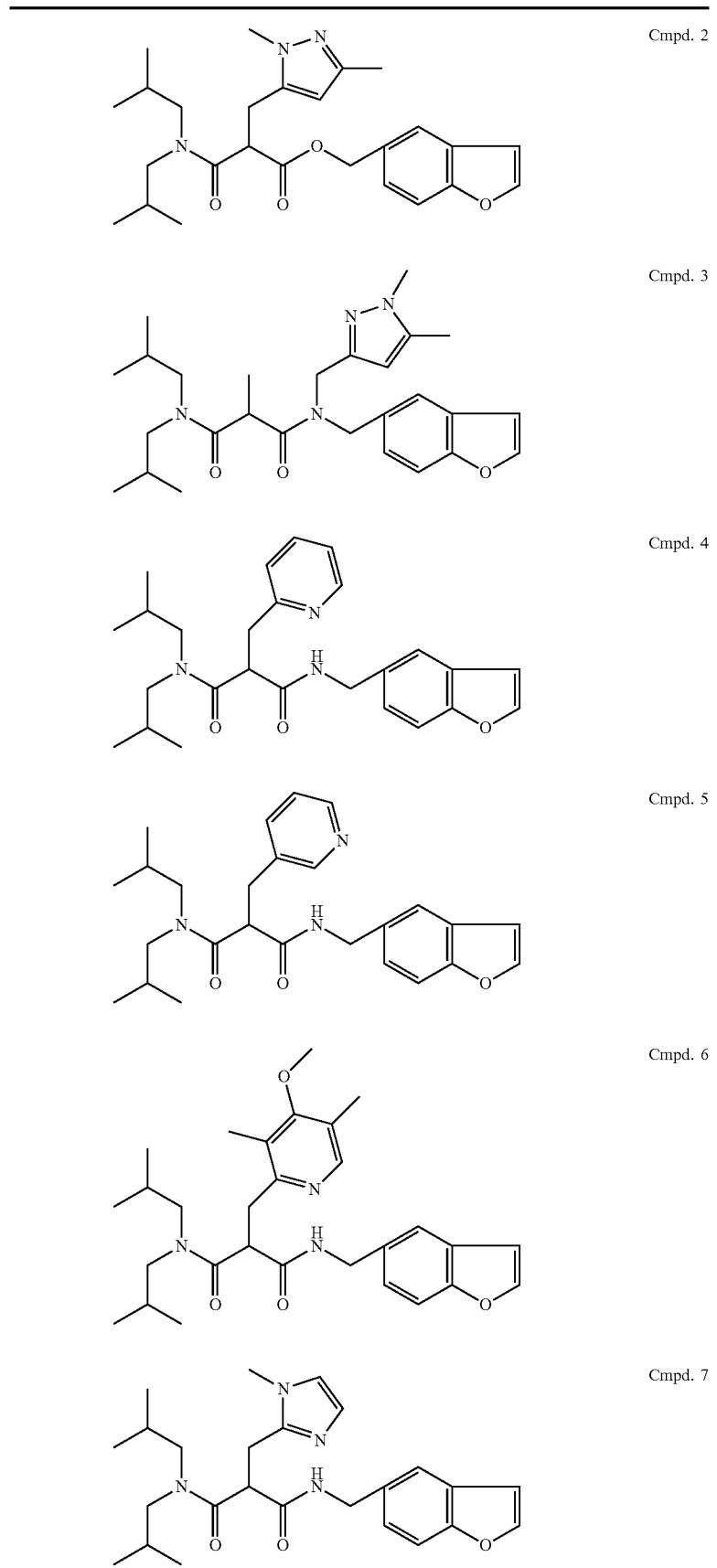

TABLE 1-continued
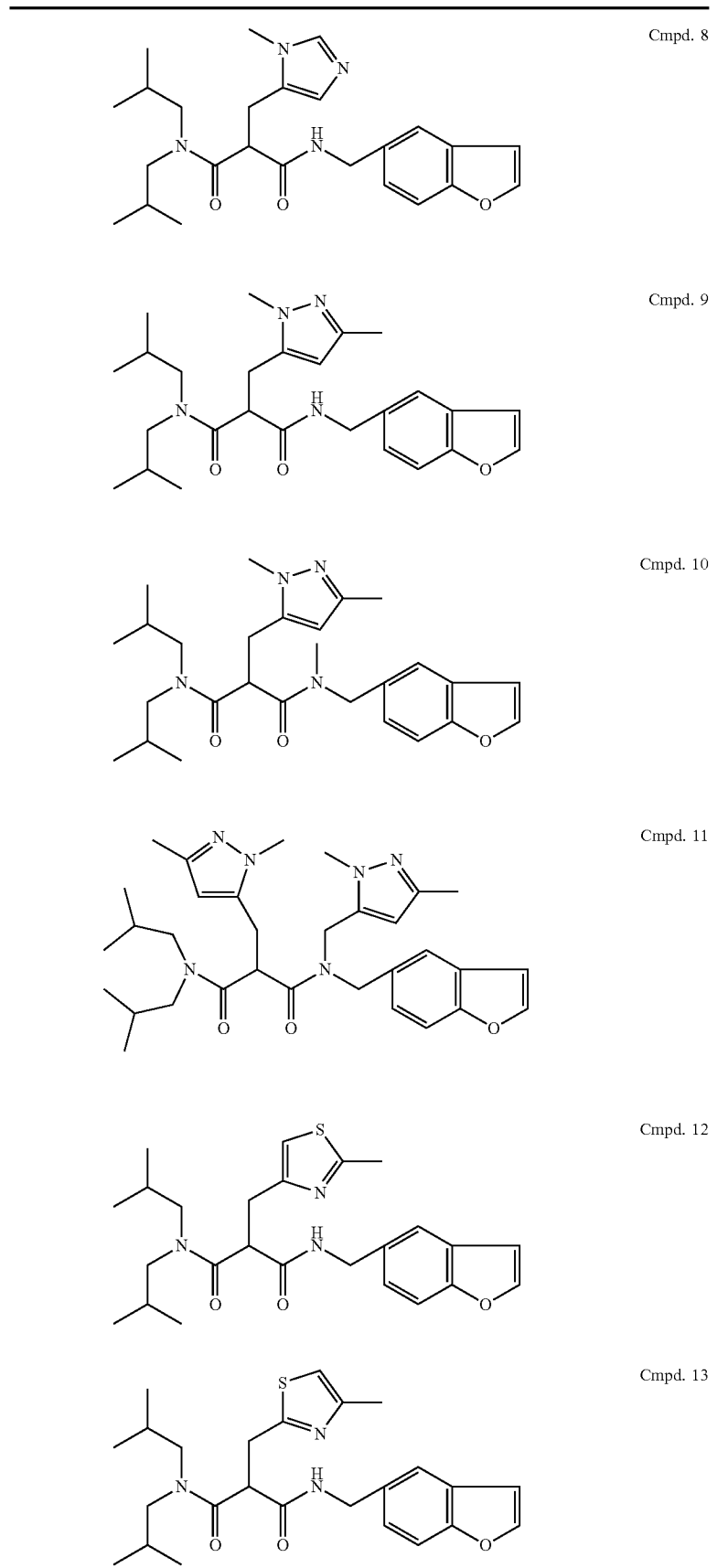

TABLE 1-continued
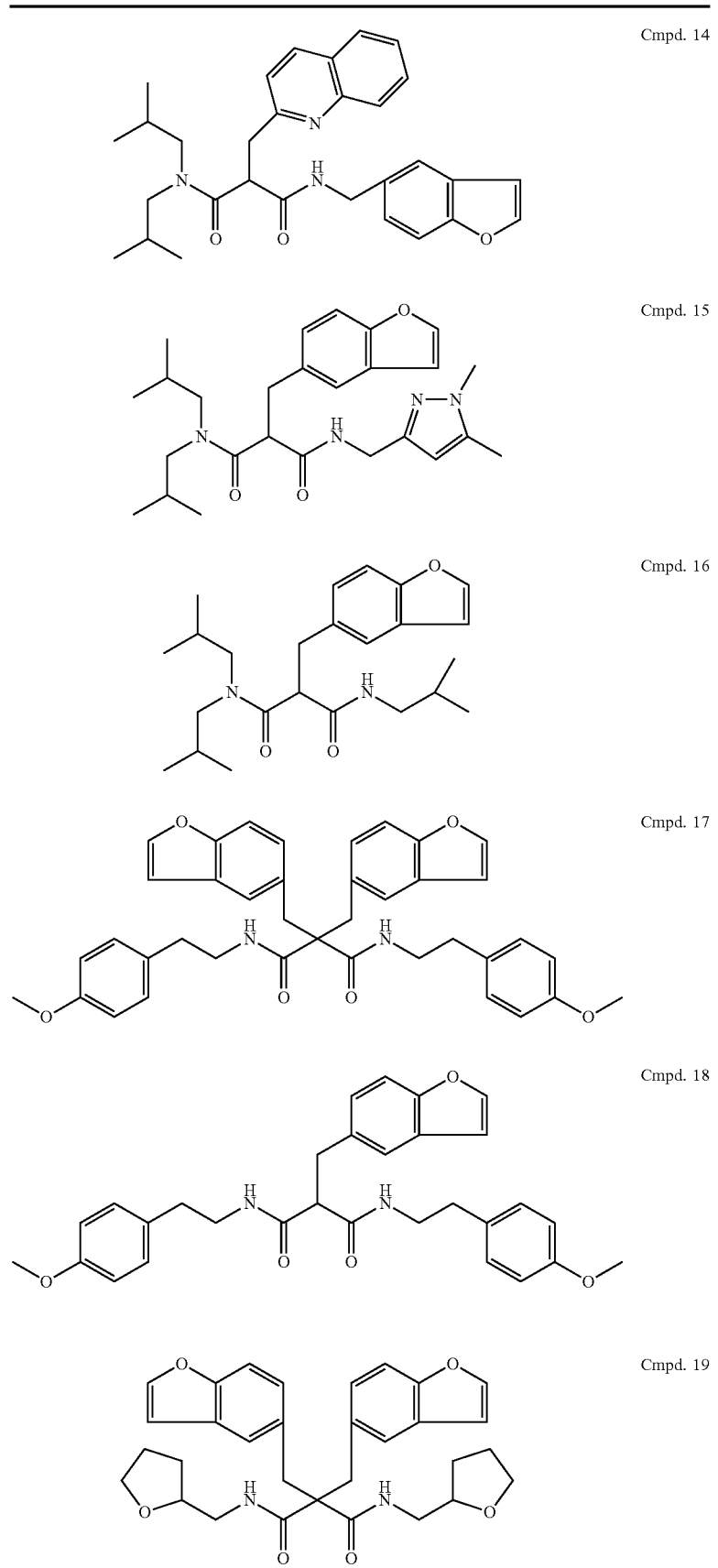

TABLE 1-continued
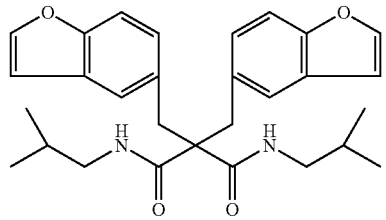 [SMILES: CC(C)CNC(=O)C(Cc1ccc2occc2c1)(Cc1ccc2occc2c1)C(=O)NCC(C)C]
Cmpd. 20
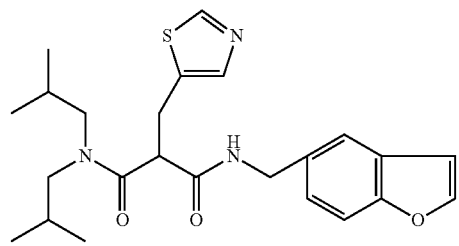 [SMILES: CC(C)CN(CC(C)C)C(=O)C(Cc1cncs1)C(=O)NCc1ccc2occc2c1]
Cmpd. 21
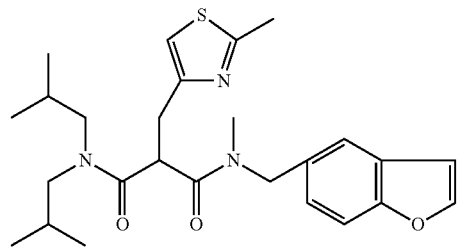 [SMILES: Cc1nc(CC(C(=O)N(C)Cc2ccc3occc3c2)C(=O)N(CC(C)C)CC(C)C)cs1]
Cmpd. 22
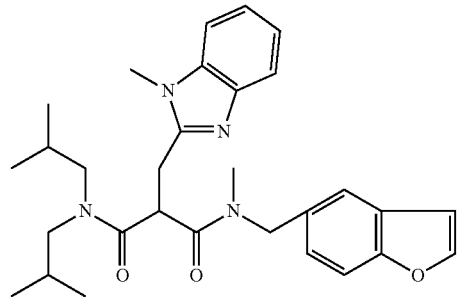 [SMILES: CC(C)CN(CC(C)C)C(=O)C(Cc1nc2ccccc2n1C)C(=O)N(C)Cc1ccc2occc2c1]
Cmpd. 23
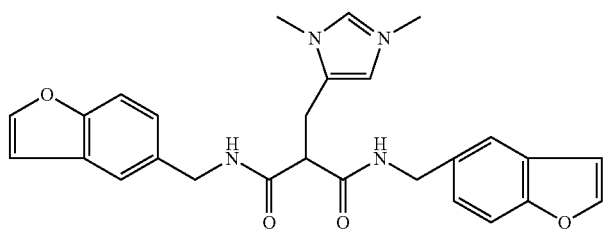
Cmpd. 24
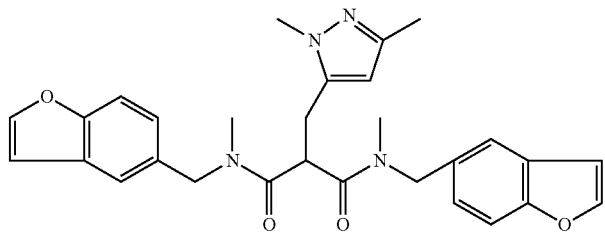 [SMILES: Cc1cc(CC(C(=O)N(C)Cc2ccc3occc3c2)C(=O)N(C)Cc2ccc3occc3c2)n(C)n1]
Cmpd. 25

TABLE 1-continued
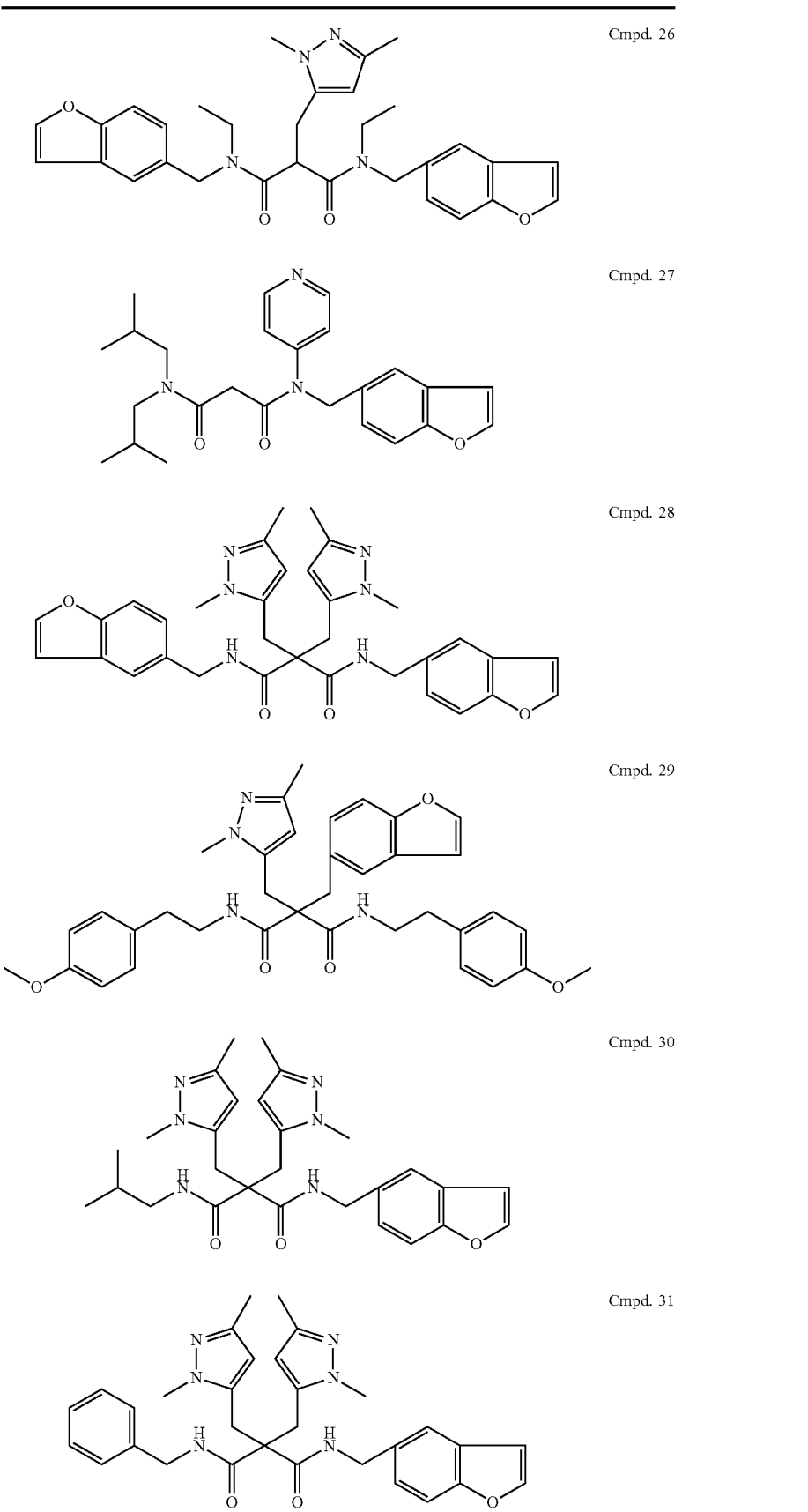
Cmpd. 26
Cmpd. 27
Cmpd. 28
Cmpd. 29
Cmpd. 30
Cmpd. 31

TABLE 1-continued
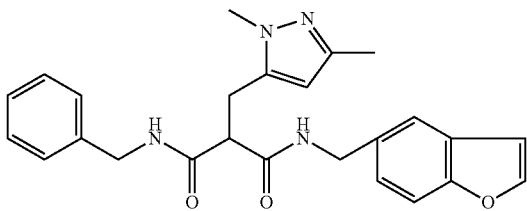 [SMILES: Cc1cc(CC(C(=O)NCc2ccccc2)C(=O)NCc2ccc3occc3c2)n(C)n1]
Cmpd. 32
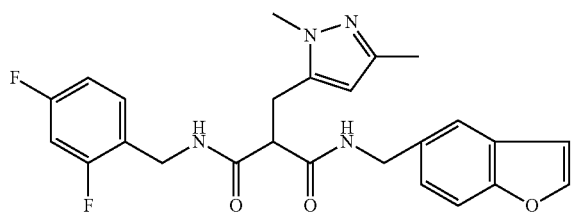 [SMILES: Cc1cc(CC(C(=O)NCc2ccc3occc3c2)C(=O)NCc2ccc(F)cc2F)n(C)n1]
Cmpd. 33
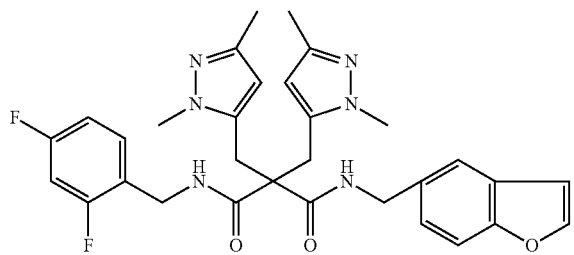 [SMILES: Cc1cc(CC(Cc2cc(C)nn2C)(C(=O)NCc2ccc3occc3c2)C(=O)NCc2ccc(F)cc2F)n(C)n1]
Cmpd. 34
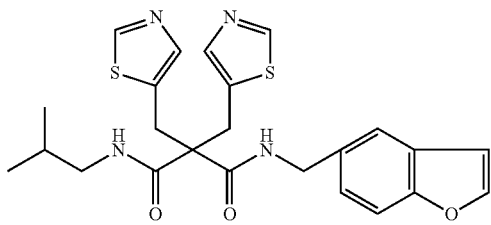 [SMILES: CC(C)CNC(=O)C(Cc1cncs1)(Cc1cncs1)C(=O)NCc1ccc2occc2c1]
Cmpd. 35
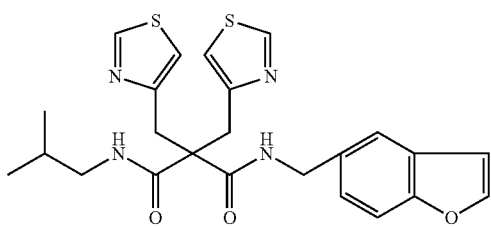 [SMILES: CC(C)CNC(=O)C(Cc1cscn1)(Cc1cscn1)C(=O)NCc1ccc2occc2c1]
Cmpd. 36
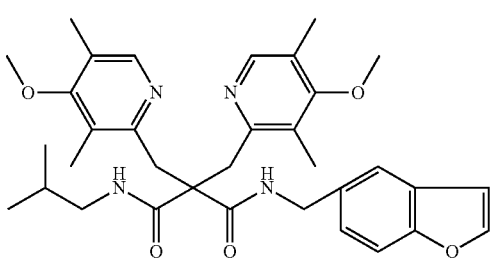 [SMILES: COc1c(C)cnc(CC(Cc2ncc(C)c(OC)c2C)(C(=O)NCc2ccc3occc3c2)C(=O)NCC(C)C)c1C]
Cmpd. 37

TABLE 1-continued

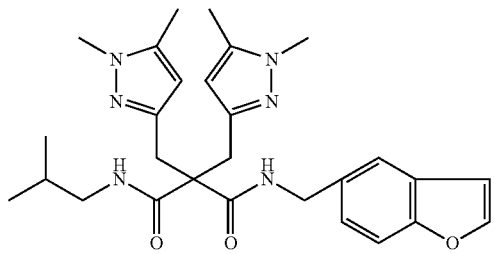 [SMILES: Cc1cc(CC(Cc2cc(C)n(C)n2)(C(=O)NCc2ccc3occc3c2)C(=O)NCC(C)C)nn1C]

Cmpd. 38

Subjects who are administered a compound of formula (I), (II), or (III) may suffer from a variety of diseases or conditions. In some embodiments the subject is a patient suffering from chronic pain, depression, epilepsy, psychosis, inflammation, cancer, cardiovascular disease, diabetes, neurodegenerative disease such as Alzheimer's disease, and/or infection. In other embodiments the subject is a patient suffering from HCV or HIV infection.

In some embodiments, the time period for administering a compound of formula (I), (II), or (III) and a drug that is metabolized by a CYP may be set or limited by the metabolism (e.g., the rate of metabolism) of the drug whose efficacy is compromised due to metabolism by CYP enzymes. In some embodiments a compound of formula (I), (II), or (III) is administered prior to, and/or substantially contemporaneously with a drug, where efficacy of the drug is compromised due to degradation by cytochrome P450 monooxygenase. In other embodiments the compound is administered at least 30 minutes, at least 1 hour, at least 2 hours, or at least 12 hours prior to administration of the drug. In another embodiment, the compound is administered substantially contemporaneously with a drug. In still another embodiment the compound and drug are co-administered to the subject.

This technology also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products can be obtained by such quaternization.

The term "pharmaceutically effective amount" or "therapeutically effective amount" or "therapeutic dose" or "efficacious dose" refers to an amount that when administered to a subject is effective in inhibiting cytochrome P450 enough to reduce or prevent the in vivo degradation of a co-administered drug and thereby improve the pharmacokinetics of the drug and/or boost its efficacy. The term "treating" as used herein refers to the alleviation of symptoms of a particular disorder in a subject, such as a human patient, or the improvement of an ascertainable measurement associated with a particular disorder. The term "prophylactically effective amount" refers to an amount effective in preventing an infection, for example an HIV infection, in a subject, such as a human patient. As used herein, a "subject" refers to a mammal, including a human.

The term "co-administered drug" or "drug" refers to a compound given to a patient or subject, which may be a human, for prophylactic or therapeutic treatment. For example, a drug or a co-administered drug may be a compound or composition listed in the U.S. Pharmacopeia, or the Physician's Desk Reference. In specific embodiments a drug or co-administered drug is selected from Cyclosporine, Tacrolimus (FK506), Sirolimus (rapamycin), Indinavir, Ritonavir, Saquinavir, Felodipine, Isradipine, Nicardipine, Nisoldipine, Nimodipine, Nitrendipine, Nifedipine, Verapamil, Etoposide, Tamoxifen, Vinblastine, Vincristine, Taxol, Atorvastatin, Fluvastatin, Lovastatin, Pravastatin, Simvastatin, Terfenadine, Loratadine, Astemizole, Alfentanil, Carbamazepine, Azithromycin, Clarithromycin, Erythromycin, Itraconazole, Rifabutin, Lidocaine, Cisapride, Sertraline, Pimozide, Triazolam, Anastrazole, Busulfan, Corticosteroids (dexamethasone, methylprednisone and prednisone), Cyclophosphamide, Cytarabine, Docetaxel, Doxorubicin, Erlotinib, Exemestane, Gefitinib, Idarubicin, Ifosphamide, Imatinib mesylate, Irinotecan, Ketoconazole, Letrozole, Paclitaxel, Teniposide, Tretinoin, Vinorelbine, telithromycin, quinidine, alprazolam, diazepam, midazolam, nelfinavir, chlorpheniramine, amlodipine, diltiazem, lercanidipine, cerivastatin, estradiol, hydrocortisone, progesterone, testosterone, alfentanyl, aripiprazole, buspirone, cafergot, caffeine, cilostazol, cocaine, codeine, dapsone, dextromethorphan, docetaxel, domperidone, eplerenone, fentanyl, finasteride, gleevec, haloperidol, irinotecan, Levo-Alpha Acetyl Methadol (LAAM), methadone, nateglinide, odansetron, propranolol, quinine, salmeterol, sildenafil, terfenadine, trazodone, vincristine, zaleplon, zolpidem., ixabepilone, Agenerase (APV), Aptivus (TPV), Crixivan (IDV), Invirase (SQV), Lexiva (FPV), Prezista (DRV), Reyataz (ATV) Viracept (NFV), Elvitegravir, Selzentry, Vicriviroc, Telaprevir, Telithromycin, tandospirone or buspirone. A drug may also be a compound that, because of its metabolism in a subject, may not otherwise be effective for treating a condition in the subject unless administered with a compound that inhibits CYP activity.

The term "antiretroviral agent" as used herein refers to a compound that inhibits the ability of a retrovirus to effectively infect a host. Antiretroviral agents can inhibit a variety of process including the replication of viral genetic materials, or entry of retroviruses into cells. In some embodiments antiretroviral agents are selected from the group consisting of: protease inhibitor, a reverse transcriptase inhibitor, and a viral fusion inhibitor. In other embodiments the antiretroviral agents are selected from the group consisting of: abacavir, didanosine, emtricitabine, lamivudine, stavudine, tenofovir, zidovudine, elvucitabine, apricitabine, zalcitabine, delavirdine, efavirenz, nevirapine, rilpivirine, etravirine, atazanavir, darunavir, fosamprenavir, indinavir, lopinavir, Kaletra, nelfinavir, ritonavir, saquinavir, tipranavir, enfuvirtide, maraviroc, vicriviroc, raltegravir, elvitegravir, interferon, albuferon, telaprevir, boceprevir, and viramidine.

The term "lipophilic group" as used herein refers to a group that, when a part of a compound, increases the affinity or propensity of the compound to bind, attach or dissolve in fat, lipid or oil rather than water. A measure of the lipophilicity or hydrophobicity of compounds of the technology can be calculated using the Hansch equation:

Log $1/C=kP$ where C is the concentration of a compound in a given solvent and P is the hydrophobicity. Details of this method can be obtained from J. Amer. Chem. Soc, 86: 5175 (1964) and *Drug Design I*, edited by E. J. Ariens, Academic Press (1971), both of which are hereby incorporated by reference in their entireties.

Examples of a typical lipophilic group include, but are not limited to, alkyl groups such as methyl, ethyl, n-propyl, isopropyl, n-butyl, isobutyl, t-butyl, n-pentyl, isopentyl, neopentyl, amyl, n-hexyl, n-heptyl, cyclohexyl, cycloheptyl, octyl, nonyl, decyl, undecyl, and dodecyl, alkenes such as ethylene, propylene, butene, pentene, hexene, cyclohexene, heptene, cycloheptene, octene, cyclooctene, nonene, decene, undecene, dodecene, 1,3-butadiene, alkynes such as propyne and butyne, aryls such as phenyl, naphthyl, anthracenyl, phenanthrenyl, fluorenyl, aralkyls such as benzyl, heterocyclyls such as tetrahydrothiophene, dihydrobenzofuran, heteroaryls such as pyrrole, furan, thiophene, pyrazole, thiazole, indole, carbazole, benzofuran, benzothiophene, indazole, benzothiazole, purine, pyridine, pyridazine, pyrazine, triazine, quinoline, acridine, isoquinoline, and phenanthroline.

For small groups containing heteroatom substituents, such as small heterocycles with a high ratio of heteroatoms to carbon atoms, the introduction of substituents that reduce the heteroatom to carbon atom ratio renders the group lipophilic. For example, a triazole ring can be rendered more lipophilic by the introduction of alkyl substituents. Similarly, non-lipophilic substituents such as hydroxy or amido can be rendered lipophilic by introducing additional carbon atoms, for example by exchanging a hydroxymethyl group to a hydroxybenzyl group, or by exchanging a carboxamido group to a dialkyl carboxamido group.

The term "substituted", whether preceded by the term "optionally" or not, and substitutions contained in formulas of this technology, include the replacement of one or more hydrogen radicals in a given structure with the radical of a specified substituent. When more than one position in a given structure can be substituted with more than one substituent selected from a specified group, the substituents can be either the same or different at every position (for example, in the moiety —N(R)$_2$, the two R substituents can be the same or different). In those embodiments where a structure can be optionally substituted, any or all of the hydrogens present may be replaced by substituents. In some embodiments, 0-3 hydrogen atoms may be replaced. In other embodiments, 0 or 1 hydrogen atoms may be replaced. Substituents advantageously enhance cytochrome P450 inhibitory activity in permissive mammalian cells, or enhance deliverability by improving solubility characteristics or pharmacokinetic or pharmacodynamic profiles as compared to the unsubstituted compound. Enhancements to cytochrome P450 inhibitory activity, deliverability and pharmacokinetic parameters achieved by the addition of substituents may result in synergistic enhancement of a compound's action and suitability for use in one or more applications.

Combinations of substituents and variables envisioned by this technology are limited to those that result in the formation of stable compounds. The term "stable", as used herein, refers to compounds that possess stability sufficient to allow manufacture, formulation, and administration to a mammal by methods known in the art. Typically, such compounds are stable at a temperature of 40° C. or less, in the absence of moisture or other chemically reactive conditions, for at least a week. In one embodiment the compounds have less than 5% degradation after storage in the dark at 40° C. or less, in the absence of moisture or other chemically reactive conditions. In another embodiment compounds have less than 10% degradation after storage in the dark at 40° C. or less, in the absence of moisture or other chemically reactive conditions.

The term "alkyl", alone or in combination with any other term, refers to a straight-chain or branched-chain saturated aliphatic hydrocarbon radical containing the specified number of carbon atoms, or where no number is specified, advantageously from 1 to about 12 or 1 to 15 carbon atoms. Examples of alkyl radicals include, but are not limited to: methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, advantageously from 2-6 or 2-10 carbon atoms. Alkenyl groups include all possible E and Z isomers unless specifically stated otherwise. Examples of alkenyl radicals include, but are not limited to, ethenyl, propenyl, isopropenyl, butenyl, isobutenyl, pentenyl, hexenyl, hexadienyl and the like.

The term "alkynyl," alone or in combination with any other term, refers to a straight-chain or branched-chain hydrocarbon radical having one or more triple bonds containing the specified number of carbon atoms, or where no number is specified, advantageously from 2 to about 10 carbon atoms. Examples of alkynyl radicals include, but are not limited to, ethynyl, propynyl, propargyl, butynyl, pentynyl and the like.

The term "alkoxy" refers to an alkyl ether radical, where the term "alkyl" is as defined above. Examples of suitable alkyl ether radicals include, but are not limited to, methoxy, ethoxy, n-propoxy, isopropoxy, n-butoxy, isobutoxy, sec-butoxy, tert-butoxy and the like.

The terms "alkylamino" or "dialkylamino" include amino radicals substituted by one or two alkyl groups, where the term "alkyl" is defined above, and the alkyl groups can be the same or different. Examples of suitable alkylamino and dialkylamino radicals include, but are not limited to, methylamino, ethylamino, isopropylamino, dimethylamino, methylethylamino, ethylbutylamino and the like.

The term "halo" or "halogen" includes fluorine, chlorine, bromine or iodine. Halo may be limited to fluorine, chlorine, and bromine or fluorine and chlorine.

The term "haloalkyl" includes alkyl groups with one or more hydrogens replaced by halogens.

The terms "aminoalkyl", "alkylaminoalkyl" or "dialkylaminoalkyl" refers to an alkyl radical as defined above in which one of the hydrogen atoms is replaced by an amino or "alkylamino" or "dialkylamino" radical as defined above.

The term "thioalkyl" includes alkyl radicals having at least one sulfur atom, where alkyl has the significance given above. An example of a thioalkyl is $CH_3SCH_2$. The definition also encompasses the corresponding sulfoxide and sulfone of this thioalkyl, $CH_3S(O)CH_2—$ and $CH_3S(O)_2CH_2—$ respectively. Unless expressly stated to the contrary, the terms "—$SO_2$-" and "—$S(O)_2$—" as used herein include sulfones or sulfone derivatives (i.e., both appended groups linked to the S), and not a sulfinate ester.

The terms "carboalkoxy" or "alkoxycarbonyl" include alkyl esters of a carboxylic acid. Examples of "carboalkoxy" or "alkoxycarbonyl" radicals include, but are not limited to, ethoxycarbonyl (or carboethoxy), Boc (or t-butoxycarbonyl), Cbz (or benzyloxycarbonyl) and the like.

The term "alkanoyl" includes acyl radicals derived from an alkanecarboxylic acid. Examples of alkanoyl radicals include, but are not limited to acetyl, propionyl, isobutyryl and the like.

The term "aryl," alone or in combination with any other term, refers to a carbocyclic aromatic radical (such as phenyl or naphthyl) containing a specified number of carbon atoms. In some embodiments aryl radicals contain from 6-16 carbon atoms, and in other embodiments aryl radicals contain from 6 to 14 or 6-10 carbon atoms in their ring structures. Aryl radicals may be optionally substituted with one or more substituents selected from alkyl, alkoxy, (for example methoxy), nitro, halo, amino, mono- or dialkylamino, carboalkoxy, cyano, thioalkyl, alkanoyl, carboxylate, and hydroxy. Examples of aryl radicals include, but are not limited to phenyl, p-tolyl, 4-hydroxyphenyl, 1-naphthyl, 2-naphthyl, indenyl, indanyl, azulenyl, fluorenyl, anthracenyl and the like.

The term "aralkyl", alone or in combination, includes alkyl radicals as defined above in which one or more hydrogen atoms is replaced by an aryl radical as defined above. Examples of aralkyl radicals include, but are not limited to benzyl, 2-phenylethyl and the like. The alkyl radical of a aralkyl group may be an alkyl radical having 1 to 4, 1 to 6, 1 to 8, 2 to 4, 2 to 6 or 2 to 8 carbon atoms.

The term "carbocycle" refers to a non-aromatic, stable 3- to 8-membered carbon ring which can be saturated, mono-unsaturated or poly-unsaturated. The carbocycle can be attached at any endocyclic carbon atom which results in a stable structure. In some embodiments, carbocycles having 5-7 carbons may be employed, whereas in other embodiments carbocycles having 5 or 6 carbon atoms may be employed.

The term "cycloalkyl", alone or in combination, includes alkyl radicals which contain from about 3 to about 8 carbon atoms and are cyclic. Examples of such cycloalkyl radicals include cyclopropyl, cyclobutyl, cyclopentyl, cyclohexyl and the like.

The term "cycloalkenyl" alone or in combination includes alkenyl radicals as defined above which contain about 3-8 carbon atoms and are cyclic.

In some embodiments of carbocycles, cycloalkyl or cycloalkenyl groups contain 3 or 4 carbon atoms in their ring structure. In other embodiments of carbocycles, cycloalkyl or cycloalkenyl groups contain 5 or 6 carbon atoms in their ring structure. In still other embodiments of carbocycles, cycloalkyl or cycloalkenyl groups contain 7 or 8 carbon atoms in their ring structure.

The term "cycloalkylalkyl" includes alkyl radicals as defined above which are substituted by a cycloalkyl radical containing from about 3 to about 8 carbon atoms in some embodiments, or from about 3 to about 6 carbon atoms in other embodiments.

The term "heterocyclyl" or "heterocyclo" or "heterocycloalkyl" refers to a stable 3-7 membered monocyclic heterocycle or 8-11 membered bicyclic heterocycle which is either saturated or partially unsaturated, and which can be optionally benzofused if monocyclic and which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, alkoxycarbonyl, arylsulfonyl, phenyl or phenylalkyl or on a tertiary nitrogen atom (i.e., +N—) by oxido and which is attached via a carbon atom. Each heterocycle consists of one or more carbon atoms and from one to four heteroatoms selected from the group consisting of nitrogen, oxygen and sulfur. As used herein, the terms "nitrogen and sulfur heteroatoms" include oxidized forms of nitrogen and sulfur, and the quaternized form of any basic nitrogen. A heterocyclyl (heterocyclo or heterocycloalkyl) radical can be attached at any endocyclic carbon or heteroatom which results in the creation of a stable structure. In some embodiments the heterocycles are 5-7 membered monocyclic heterocycles, and 8-10 membered bicyclic heterocycles. Examples of such groups are imidazolinyl, imidazolidinyl, indazolinyl, perhydropyridazyl, pyrrolinyl, pyrrolidinyl, piperidinyl, pyrazolinyl, piperazinyl, morpholinyl, thiamorpholinyl, thiazolidinyl, thiamorpholinyl sulfone, oxopiperidinyl, oxopyrrolidinyl, oxoazepinyl, tetrahydropyranyl, tetrahydrofuranyl, dioxolyl, dioxinyl, benzodioxolyl, dithiolyl, tetrahydrothienyl, sulfolanyl, dioxanyl, dioxolanyl, tetahydrofurodihydrofuranyl, tetrahydropyranodihydrofuranyl, dihydropyranyl, tetradyrofurofuranyl and tetrahydropyranofuranyl.

The term "heteroaryl" refers to stable 5-6 membered monocyclic or 8-11 membered bicyclic or 13-16 membered tricyclic aromatic heterocycles where heterocycle is as defined above. In some embodiments, heteroatoms present in heteroaryl radicals are limited to one or more independently selected O, N or S atoms. Non-limiting examples of such groups include imidazolyl, quinolyl, isoquinolyl, indolyl, indazolyl, pyridazyl, pyridyl, pyrrolyl, pyrazolyl, pyrazinyl, quinoxalinyl, pyrimidinyl, furyl, thienyl, triazolyl, thiazolyl, carbolinyl, tetrazolyl, benzofuranyl, oxazolyl, benzoxazolyl, benzimidazolyl, benzthiazolyl, isoxazolyl, isothiazolyl, furazanyl, thiadiazyl, acridinyl, phenanthridinyl, and benzocinnolinyl.

The term "heterocycloalkylalkyl" refers to an alkyl radical as defined above which is substituted by a heterocycloalkyl radical as defined above. The alkyl radical of a heterocycloalkylalkyl group may be an alkyl radical having 1 to 4, 1 to 6, 1 to 8, 2 to 4, 2 to 6 or 2 to 8 carbon atoms.

The term "heteroaralkyl" alone or in combination, includes alkyl radicals as defined above in which one or more hydrogen atom is replaced by a heteroaryl group as defined above. The alkyl radical of a heteroaralkyl group may be an alkyl radical having 1 to 4, 1 to 6, 1 to 8, 2 to 4, 2 to 6 or 2 to 8 carbon atoms.

As used herein, the compounds of this technology (e.g., compounds of formula (I) (II) or (III) are defined to include pharmaceutically acceptable derivatives or prodrugs thereof. A "pharmaceutically acceptable derivative or prodrug" includes a pharmaceutically acceptable salt, ester, salt of an ester, or other derivative of a compound of this technology which, upon administration to a recipient, is capable of providing (directly or indirectly) a compound of this technology. In some embodiments it is desirable to employ derivatives and prodrugs that increase the bioavailability of the compounds of this technology when such compounds are administered to a mammal (e.g., by allowing an orally administered compound to be more readily absorbed into the blood) or which enhance delivery of the parent compound to a biological compartment (e.g., the brain or lymphatic system) relative to the parent species. Examples of prodrugs of hydroxy containing compounds are amino acid esters or phosphonate or phosphate esters that can be cleaved in vivo hydrolytically or enzymatically to provide the parent compound. These have the advantage of providing potentially improved solubility.

The compounds of this technology (e.g., compounds of formula (I) (II) or (III) can contain one or more asymmetric carbon atoms and thus occur as racemates and racemic mixtures, single enantiomers, diastereomeric mixtures and individual diastereomers. All such isomeric forms of these compounds are expressly included in the technology described herein. Each stereogenic carbon can be of the R or S configuration. Although the specific compounds exemplified in this application can be depicted in a particular stereochemical configuration, compounds having either the opposite stereochemistry at any given chiral center or mixtures thereof are also envisioned. Thus, the compounds provided herein may be enantiomerically pure, or be stereoisomeric or diastereomeric mixtures.

It is also to be understood that the compounds provided herein may have tautomeric forms. All such tautomeric forms are included within the scope of the instant disclosure.

Also included in the present application are one or more of the various polymorphs of the compounds. A crystalline compound disclosed in the present application may have a single or may have multiple polymorphs, and these polymorphs are intended to be included as compounds of the present application. Also, where a single polymorph is noted, the polymorph may change or interconvert to one or more different polymorphs, and such polymorph or polymorph mixtures are included in the present application.

Preparation of Compounds

The compounds described herein can be prepared according to synthetic methods known in the art set forth, for example, in U.S. Pat. No. 6,319,946 to Hale et al., W02008022345A2 (Eissenstat et al.), and in *J. Med. Chem.* 36, 288-291 (1993), the disclosures of which are incorporated herein by reference in their entireties, together with procedures of the type described below. Reactions and processes for obtaining the compounds, particularly the formation of ester and amide linkages, may also be found in treatises and text, including, but not limited to, *Advanced Organic Synthesis*, 4th Edition, J. March, John Wiley & Sons, 1992 or *Protective Groups in Organic Synthesis* 3rd Edition, T. W. Green & P. G. M. Wuts, John Wiley & Sons, 1999, each of which is hereby incorporated by reference.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's *Reagents for Organic Syntheses*, Volumes 1-85 (John Wiley and Sons); Rodd's *Chemistry of Carbon Compounds*, Volumes 1-5 and Supplementals (Elsevier Science Publishers, 1989); *Organic Reactions*, Volumes 1-71 (John Wiley and Sons), *Advanced Organic Synthesis,* 4th Edition, J. March, John Wiley & Sons, 1992, and Larock's *Comprehensive Organic Transformations* (VCH Publishers Inc., 1989).

Protective groups, such as those described in *Protective Groups in Organic Synthesis* 3rd Edition, T. W. Green & P. G. M. Wuts, John Wiley & Sons, 1999 may be employed for a variety of purposes in the preparation of compounds encompassed by this disclosure. They may be employed to control the number or placement of substituents, or to protect functionalities that are otherwise unstable to reaction conditions employed for the introduction or modification of other substituents in a molecule. Where employed, such protective groups may be removed by suitable means. Alternatively, where the protective group is desirable in the product they may be introduced and not removed.

While compounds encompassed by this disclosure may be prepared by a variety of methods known in the art, they may often be prepared from derivatives of malonic acid such as malonyl dichloride, or from methyl 3-chloro-3-oxopropionate such as outlined in Scheme I.

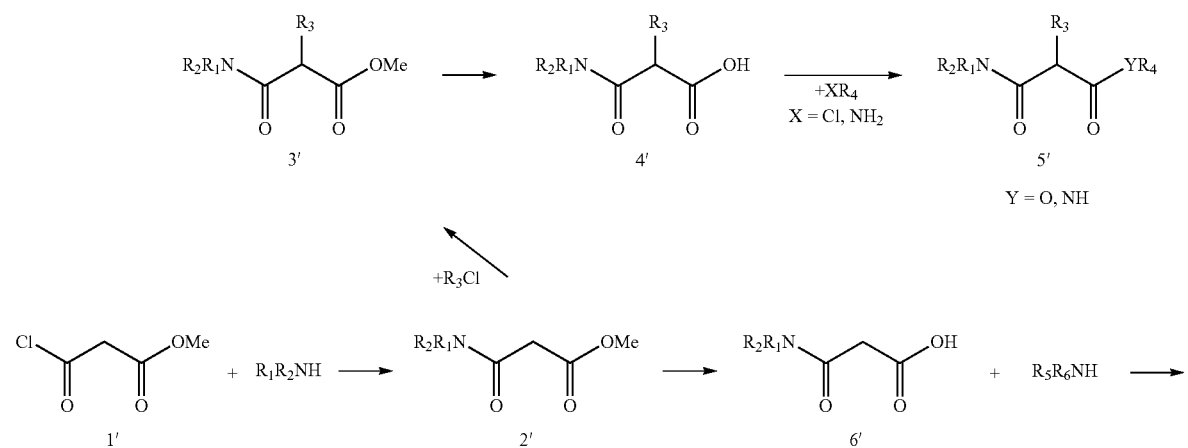

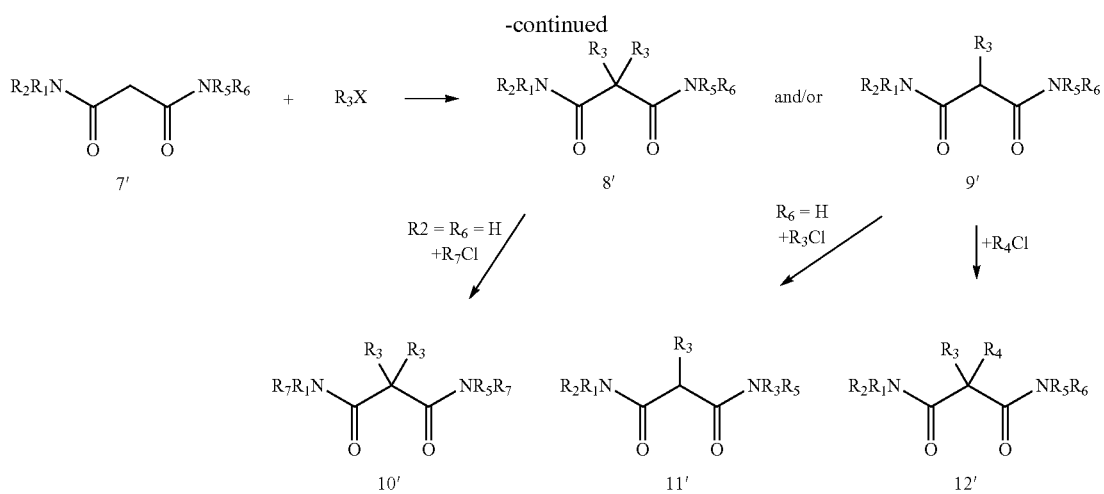

In the method outlined in Scheme I, methyl 3-chloro-3-oxopropionate 1' is reacted with a primary or secondary amine in dichloromethane to provide the corresponding amide-ester 2'. Ester 2' is hydrolyzed using lithium hydroxide in methanol/water and then acidified to provide the carboxylic acid 6 which is then condensed with a new amine using standard amide forming conditions such as 1-hydroxybenzotriazole (HOBt) and 1-ethyl-3-(3-dimethylaminopropyl)carbodiimide (EDC) in a two phase dichloromethane/water system or 2-(1H-7-Azabenzotriazol-1-yl)-1,1,3,3-tetramethyl uronium hexafluorophosphate (HATU) and N,N-diisopropylethylamine (DIPEA) in dichloromethane (DCM) to provide the malonamide 7'. The malonamide is then treated with sodium hydride in dimethylformamide (DMF) and alkylated with a substituted alkyl halide to provide the 2,2-dialkyl malonamide 8' or 2-monoalkyl malonamide 9'. Malonamide 8' ($R_2=R_6=H$) can be further alkylated to N,N-dialkylated malonamide 10'. 2-Monoalkylated malonamide 9' can be further alkylated to give the C,N-dialkylated malonamide 11' or C,C-dialkylated malonamide 12'. Alternatively, ester 2' is first alkylated to give the 2-alkylated methyl malonate 3'. After hydrolysis and acidification, malonic acid 4' is reacted with an alkyl halide or condensed with a new amine to provide malonamide 5'.

In other embodiments, where Q is —$NR^5R^6$ (i.e., compounds of formula (II)) and the compound contains symmetrical substitutes on the amide nitrogens, the compounds may be prepared by reacting malonyl dichloride with a suitably substituted primary or secondary amine.

Substituents at $R^3$ and $R^4$ may be introduced by a variety of means that will be apparent to those of skill in the art. For example substituents at $R^3$ and $R^4$ may be introduced by employing starting materials bearing the desired groups or suitably protected precursors thereof. For example methyl groups at $R^3$ and $R^4$ may be included in the final compound by employing 2,2-dimethylmalonoyl dichloride as a starting material. Alternatively, substituents can be introduced by reacting compounds bearing a 1,3-dicarbonyl group with a suitable halogenated compound, such as an alkyl chloride, to introduce groups that will be present at $R^3$ and/or $R^4$.

Where Q is —$OR^5$, various esters may be formed by reactions known in the art. For example, various esters can be prepared by condensation of alcohols with a carboxylic acid or by transesterification reactions.

Assessment of Compounds

The potency of the compounds can be measured using assays, for example, an in vitro fluorometric assay. Typically, the ability of a test compound to inhibit P450 is assayed by determining the concentration of the test compound required to decrease the rate of metabolism of a CYP substrate (also referred to herein as reference compound) by half. The CYP substrate can be, for example, dibenzylfluorescein. The ability of a test compound to inhibit the rate of metabolism of a reference compound by half is known as the $IC_{50}$ value. Human liver microsomes can be used for this purpose. Test compounds can be diluted with a suitable solvent, such as acetonitrile, in wells of a micro-titer plate. Known cytochrome P450 inhibitors such as ritonavir and ketoconazole can be used as references. A suitable buffer solution and NADPH or an NADPH generating system such as, for example, G6P dehydrogenase can be used. After mixing the inhibitors with the buffer and NADPH system, the plates can be incubated for a suitable time at a suitable temperature. A solution containing human liver microsomes can be added. A buffer containing a fluorogenic substrate, such as dibenzylfluorescein, can be added and the plates allowed to incubate for a suitable time at a suitable temperature. The $IC_{50}$ values for the test compounds can be measured by determining the amount of fluorescence in each well and analyzing the values using commercially available software programs such as, for example, Grafit® (Erithacus Software Ltd., Surrey, U.K.).

Increasing the Half-Life of Therapeutics by Preventing their Metabolism by Cytochrome P450 Enzymes CYP enzymes are responsible for the metabolic degradation of a variety of drug molecules (therapeutics). In many instances, those enzymes may largely determine the pharmacokinetics observed for drug molecules and control their bioavailability. Where CYP enzymes contribute to the metabolism of compounds, compositions that can inhibit CYP enzymes can improve the pharmacokinetics and bioavailability of such drugs.

In certain embodiments, the technology provides methods for inhibiting cytochrome P450 monooxygenase by administering to a patient one or more compounds described herein. The compound can function as a potent cytochrome P450 inhibitor and can improve the pharmacokinetics of a drug (or a pharmaceutically acceptable salt thereof) which is metabolized by cytochrome P450 monooxygenase. The compound or its pharmaceutically acceptable salt can be administered by itself or in combination with another drug. When administered in combination, the two therapeutic agents (compound and drug) can be formulated as separate compositions which are administered at the same time or at different times, or the two therapeutic agents can be administered as a single composition.

The compounds of the technology are effective for inhibiting a variety of CYP enzymes. In particular, many of the compounds are highly potent inhibitors of CYP3A4, which is responsible for degrading many pharmaceutically important drugs. Use of the compounds of the technology therefore permits reduced rates of drug degradation and consequently extended durations of action in vivo. Consequently, these compounds are useful for "boosting" the activities of a variety of drugs, including, but not limited to, HIV protease inhibitors by inhibiting CYP3A4-mediated degradation of those inhibitors.

Drugs which are metabolized by cytochrome P450 monooxygenase and which benefit from coadministration with a compound of the technology include, but are not limited to, the immunosuppressants cyclosporine, FK-506 and rapamycin, the chemotherapeutic agents taxol and taxotere, the antibiotic clarithromycin and the HIV protease inhibitors A-77003, A-80987, indinavir, saquinavir, amprenavir, nelfinavir, fosamprenavir, lopinavir, atazanavir, darunavir, tipranavir, DMP-323, XM-450, BILA 2011 BS, BILA 1096 BS, BILA 2185 BS, BMS 186,318, LB71262, SC-52151, SC-629 (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), PPL-100, SPI-256 and KNI-272.

In other examples, the drug may be a tyrosine kinase inhibitor, such as Gleevec (imatinib), Erlotinib, Sorafenib, Sunitinib, dasitinib, lapatinib, and the like. Other kinase inhibitors, such as serine/threonine kinase inhibitors, also may be "boosted." Suitable kinase inhibitors for boosting also are described in Kéri et al.; "*Signal Transduction Therapy with Rationally Designed Kinase Inhibitors*," Current Signal Transduction Therapy, 1, 67-95 67 (2006). The drug may also be an HSP90 inhibitor such as geldanamycin, herbimycin, and others, as described by Workman et al.: "*Drugging the cancer chaperone HSP90: Combinatorial therapeutic exploitation of oncogene addiction and tumor stress*" Workman, Ann N Y Acad Sci. 1113:202-216 (2007). In other examples, the drug may be an inhibitor of HCV NS3 protease, NS4a cofactor, NS4B, NS5a replicase or NS5B polymerase. Drugs for treating HIV include, in addition to HIV protease inhibitors, inhibitors of CD4-gp120 interaction, CCR5 and CRCX4 coreceptors, and inhibitors of the LEDGF-integrase interaction.

Protease inhibitors and non-nucleoside reverse transcriptase inhibitors currently indicated for use in treatment of HIV or HCV are typically good substrates of cytochrome p450 enzymes; in particular, they are metabolized by CYP3A4 enzymes (see e.g., Sahai, AIDS 10 Suppl 1:521-5, 1996) with possible participation by CYP2D6 enzymes (Kumar et al., *J. Pharmacol. Exp. Ther.* 277(1): 423-31, 1996). The compounds described herein can block the action and up-regulation of these enzymes, thus reducing the metabolism of the protease inhibitors, allowing for lower doses, and reduction of sometimes serious side effects.

Some embodiments described herein are directed to methods for improving the pharmacokinetics of an HIV protease inhibitor (or a pharmaceutically acceptable salt thereof), which is metabolized by cytochrome P450 monooxygenase. Those methods comprise co-administering to a subject or patient (e.g., a human being) a compound of the technology or a pharmaceutically acceptable salt or co-crystal thereof and an HIV protease inhibitor. Such a combination of a compound of the technology (e.g., a compound of formula (I), (II) or (III)), or a pharmaceutically acceptable salt thereof, and an HIV protease inhibitor, or a pharmaceutically acceptable salt thereof, which is metabolized by cytochrome P450 monooxygenase is useful for inhibiting HIV protease in humans. The combination is also useful for the inhibition, treatment or prophylaxis of an HIV infection or AIDS (acquired immune deficiency syndrome) in humans. When administered in combination, the two therapeutic agents can be formulated as separate compositions which are administered at the same time or at different times, or the two therapeutic agents can be administered as a single composition. In some embodiments the HIV protease inhibitors are selected from A-77003, A-80987, amprenavir atazanavir, darunavir, fosamprenavir, indinavir, lopinavir, nelfinavir, ritonavir, saquinavir, tipranavir, DMP-323, XM-450, BILA 2011 BS, BILA 1096 BS, BILA 2185 BS, BMS 186,318, LB71262, SC-52151, SC-629, (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), PPL-100, SPI-256 or KNI-272.

In other embodiments, the drug may be a tyrosine kinase inhibitor, such as Gleevec (imatinib), Erlotinib, Sorafenib, Sunitinib, dasitinib, lapatinib, and the like. Other kinase inhibitors, such as serine/threonine kinase inhibitors, also may be "boosted." Suitable kinase inhibitors for boosting also are described in Kéri et al.; "*Signal Transduction Therapy with Rationally Designed Kinase Inhibitors*," Current Signal Transduction Therapy, 1, 67-95 67 (2006). The drug may also be an HSP90 inhibitor such as geldanamycin, herbimycin, and others, as described by Workman et al.: "*Drugging the cancer chaperone HSP90: Combinatorial therapeutic exploitation of oncogene addiction and tumor stress*" Workman, Ann N Y Acad Sci. 1113:202-216 (2007). In other examples, the drug may be an inhibitor of HCV NS3 protease, NS4a cofactor, NS4B, NS5a replicase or NS5B polymerase. Drugs for treating HIV include, in addition to HIV protease inhibitors, inhibitors of CD4-gp120 interaction, CCR5 and CRCX4 coreceptors, and inhibitors of the LEDGF-integrase interaction.

Methods of Administration.

The compounds of the technology can be administered in the form of pharmaceutically acceptable salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

Other pharmaceutically acceptable salts include salts with an inorganic base, organic base, inorganic acid, organic acid, or basic or acidic amino acid. Inorganic bases which form the pharmaceutically acceptable salts include alkali metals such as sodium or potassium, alkali earth metals such as calcium and magnesium, aluminum, and ammonia. Organic bases which form pharmaceutically acceptable salts include trimethylamine, triethylamine, pyridine, picoline, ethanolamine, diethanolamine, triethanolamine, dicyclohexylamine. Inorganic acids which form pharmaceutically acceptable salts include hydrochloric acid, hydroboric acid, nitric acid, sulfuric acid, and phosphoric acid. Organic acids appropriate to form salts include formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Basic amino acids used to form salts include arginine, lysine and ornithine. Acidic amino acids used to form salts include aspartic acid and glutamic acid.

The compounds described herein, including compound formula (I), (II), (III) and salts thereof, may also be prepared and administered as a composition comprising a co-crystals with other compounds (co-crystal formers). "Co-crystal" as used herein means a crystalline material comprised of two or more unique solids at room temperature, each containing distinctive physical characteristics, such as structure, melting point and heats of fusion. Co-crystals are described, for example, in U.S. Pub. No.: 20070026078 A1, which is incorporated by reference in its entirety. They are also described in N. A. Meanwell, *Annual Reports in Medicinal Chemistry*, Volume 43, 2008, and D. P. McNamara, Pharmaceutical Research, Vol. 23, No. 8, 2006, which is incorporated by reference in its entirety.

The technology also contemplates compositions which can be administered orally or non-orally in the form of, for example, granules, powders, tablets, capsules, syrup, suppositories, injections, emulsions, elixirs, suspensions or solutions, by mixing these effective components, individually or simultaneously, with pharmaceutically acceptable carriers, excipients, binders, diluents or the like.

As a solid formulation for oral administration, the composition can be in the form of powders, granules, tablets, pills and capsules. In these cases, the compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as paraben or sorbic acid, an anti-oxidant such as ascorbic acid, tocopherol or cysteine, a disintegrator, a binder, a thickening agent, a buffer, a sweetener, a flavoring agent and a perfuming agent. Tablets and pills can further be prepared with enteric coating.

Examples of liquid preparations for oral administration include pharmaceutically acceptable emulsions, syrups, elixirs, suspensions and solutions, which can contain an inactive diluent, for example, water.

As used herein, "non-orally" includes subcutaneous injection, intravenous injection, intramuscular injection, intraperitoneal injection or instillation. Injectable preparations, for example sterile injectable aqueous suspensions or oil suspensions can be prepared by known procedures in the fields concerned, using a suitable dispersant or wetting agent and suspending agent. The sterile injections can be, for example, a solution or a suspension, which is prepared with a nontoxic diluent administrable non-orally, such as an aqueous solution, or with a solvent employable for sterile injection. Examples of usable vehicles or acceptable solvents include water, Ringer's solution and an isotonic aqueous saline solution. Further, a sterile, non-volatile oil can usually be employed as solvent or suspending agent. A non-volatile oil and a fatty acid can be used for this purpose, including natural or synthetic or semi-synthetic fatty acid oil or fatty acid, and natural or synthetic mono- or di- or tri-glycerides.

The pharmaceutical compositions can be formulated for nasal aerosol or inhalation and can be prepared as solutions in saline, and benzyl alcohol or other suitable preservatives, absorption promoters, fluorocarbons, or solubilizing or dispersing agents.

Rectal suppositories can be prepared by mixing the drug with a suitable vehicle, for example, cocoa butter and polyethylene glycol, where the vehicle is in the solid state at ordinary temperatures and in the liquid state at body temperatures, where melting releases the drug.

The pharmaceutical composition can be easily formulated for topical administration with a suitable ointment containing one or more of the compounds suspended or dissolved in a carrier, which include mineral oil, liquid petroleum, white petroleum, propylene glycol, polyoxyethylene, polyoxypropylene compound, emulsifying wax and water. In addition, topical formulations can be formulated with a lotion or cream containing the active compound suspended or dissolved in a carrier. Suitable carriers include mineral oil, sorbitan monostearate, polysorbate 60, cetyl esters wax, cetaryl alcohol, 2-octyldodecanol, benzyl alcohol and water.

In some embodiments, the pharmaceutical compositions can include α-, β-, or γ-cyclodextrins or their derivatives. In certain embodiments, co-solvents such as alcohols can improve the solubility and/or the stability of the compounds in pharmaceutical compositions. In the preparation of aqueous compositions, addition salts of the compounds can be suitable due to their increased water solubility.

Appropriate cyclodextrins are α-, β-, or γ-cyclodextrins (CDs) or ethers and mixed ethers thereof where one or more of the hydroxy groups of the anhydroglucose units of the cyclodextrin are substituted with $C_1$-$C_6$alkyl, such as methyl, ethyl or isopropyl, e.g., randomly methylated β-CD; hydroxy $C_{1-6}$alkyl, particularly hydroxyethyl, hydroxypropyl or hydroxybutyl; carboxy $C_1$-$C_6$alkyl, particularly carboxymethyl or carboxyethyl; $C_1$-$C_6$alkyl-carbonyl, particularly acetyl; $C_1$-$C_6$alkyloxycarbonyl$C_1$-$C_6$alkyl or carboxy$C_1$-$C_6$alkyloxy$C_1$-$C_6$alkyl, particularly carboxymethoxypropyl or carboxyethoxypropyl; $C_1$-$C_6$alkylcarbonyloxy$C_1$-$C_6$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, hydroxypropyl-γ-CD and (2-carboxymethoxy)propyl-β-CD, and in particular 2-hydroxy-propyl-β-CD (2-HP-β-CD).

The term "mixed ether" denotes cyclodextrin derivatives where at least two cyclodextrin hydroxy groups are etherified with different groups such as, for example, hydroxypropyl and hydroxyethyl.

The compounds can be formulated in combination with a cyclodextrin or a derivative thereof as described in U.S. Pat. No. 5,707,975. Although the formulations described therein are with antifungal active ingredients, they are equally relevant for formulating compounds and compositions of the technology described herein (e.g. compounds of formula (I), (II), (III) and salts thereof). The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. The formulations can also be rendered more palatable by adding pharmaceutically acceptable sweeteners and/or flavors.

Other convenient ways to enhance the solubility of the compounds of the technology in pharmaceutical compositions are described in WO 94/05263, WO 98/42318, EP-A-499,299 and WO 97/44014, all incorporated herein by reference.

In some embodiments, the compounds can be formulated in a pharmaceutical composition comprising a therapeutically effective amount of particles consisting of a solid dispersion comprising a compound of formula I, and one or more pharmaceutically acceptable water-soluble polymers.

The term "solid dispersion" defines a system in a solid state comprising at least two components, where one component is dispersed more or less evenly throughout the other component or components. When the dispersion of the components is such that the system is chemically and physically uniform or homogenous throughout or consists of one phase as defined in thermodynamics, such a solid dispersion is referred to as "a solid solution". Solid solutions are one preferred physical system because the components therein are usually readily bioavailable to the organisms to which they are administered.

The term "solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa*s when dissolved in a 2% aqueous solution at 20° C.

Water-soluble polymers include hydroxypropyl methylcelluloses (HPMC). HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation.

It can further be convenient to formulate the compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Surfactant surface modifiers include nonionic and anionic surfactants.

The compounds can also be incorporated in hydrophilic polymers and applied as a film over many small beads, thus yielding a composition with good bioavailability which can conveniently be manufactured and which is suitable for preparing pharmaceutical dosage forms for oral administration. The beads comprise a central, rounded or spherical core, a coating film of a hydrophilic polymer and an antiretroviral agent and a seal-coating polymer layer. Materials suitable for use as cores are pharmaceutically acceptable and have appropriate dimensions and firmness. Examples of such materials are polymers, inorganic substances, organic substances, saccharides and derivatives thereof. The route of administration can depend on the condition of the subject, co-medication and the like.

Dosages of the compounds and compositions described herein are dependent on age, body weight, general health conditions, sex, diet, dose interval, administration routes, excretion rate, combinations of drugs and conditions of the diseases treated, while taking these and other necessary factors into consideration. Generally, dosage levels of between about 10 µg per day to about 5000 mg per day, preferably between about 25 mg per day to about 1000 mg per day of the compounds of the technology are useful for the inhibition of CYP enzymes. Typically, the pharmaceutical compositions of this technology will be administered from about 1 to about 3 times per day or alternatively, as a continuous infusion. Such administration can be used as a chronic or acute therapy.

The amount of active ingredient that can be combined with the carrier materials to produce a single dosage form will vary depending upon the host treated and the particular mode of administration. A typical preparation will contain from about 5% to about 95% active compound (w/w). In some embodiments, such preparations contain from about 20% to about 80% active compound.

While these dosage ranges can be adjusted by a necessary unit base for dividing a daily dose, as described above, such doses are decided depending on the diseases to be treated, conditions of such diseases, the age, body weight, general health conditions, sex, diet of the patient then treated, dose intervals, administration routes, excretion rate, and combinations of drugs, while taking these and other necessary factors into consideration. For example, a typical preparation will contain from about 5% to about 95% active compound (w/w). Preferably, such preparations contain from about 10% to about 80% active compound. The desired unit dose of the composition of this technology is administered once or multiple times daily.

In some embodiments, the technology contemplates compositions and formulations comprising one or more of the compounds in combination with one or more other drugs that can be metabolized or degraded by CYP.

The CYP inhibitors of this technology can be administered to a patient either as a single agent (for use with a separate dose of another drug) or in a combined dosage form with at least one other drug. Additional drugs also can be used to increase the therapeutic effect of these compounds.

The compounds of this technology can be administered to patients being treated with a drug that is metabolized by a CYP enzyme. Such drugs include, but are not limited to, anesthetics such as ropivacaine, enflurane, halothane, isoflurane, methoxyflurane, and sevoflurane; antiarrhythmics such as mexiletine; antidepressants such as amitriptyline, clomipramine, fluvoxamine, bupropion, and imipramine; anti-epileptics such as diazepam, phenytoin, S-mephenytoin, and phenobarbitone; antihistamines such as astemizole, chlorpheniramine, and terfenadine; antipsychotics such as clozapine, olanzapine, and haloperidol; beta blockers such as carvedilol, S-metoprolol, propafenone, and timolol; calcium channel blockers such as amlodipine, diltiazem, felodipine, lercanidipine, nifedipine, nisoldipine, nitrendipine, and verapamil; hypoglycemic agents such as tolbutamide and glipizide; immune modulators such as cyclosporine and tacrolimus; muscle relaxants such as cyclobenzaprine, tizanidine, and carisoprodol; steroids such as estradiol; antimigraine agents such as zolmitriptan; agents used to treat breathing aliments such as zileuton and theophylline; agents used to treat Alzheimer's disease such as tacrine; agents used to treat pain such as naproxen and acetaminophen; agents used to treat amyotrophic lateral sclerosis such as riluzole; anti-nausea agents such as ondansetron; chemotherapeutics such as paclitaxel, ifosfamide, and cyclophosphamide; loop diuretics such as torsemide; antidiabetic agents such as repaglinide; statins such as cerivastatin; antimalarial agents such as amodiaquine; proton pump inhibitors such as lansoprazole, omeprazole, pantoprazole, and rabeprazole; and sulfonylureas such as glyburide, glibenclamide, glipizide, glimepiride, and tolbutamide. Patients being treated with a protease inhibitor, a reverse transcriptase inhibitor, a viral fusion inhibitor, or an integrase inhibitor can also be treated with the compounds provided herein. The CYP inhibitors provided herein can be co-administered with the other drug(s). The compounds of the technology can also be administered in combination with other cytochrome P450 inhibitors (e.g., ritonavir), immuno-modulators (e.g., bropirimine, anti-human alpha interferon antibody, IL-2, interferon alpha, and HE-2000), with antibiotics (e.g., pentamidine isothiorate) cytokines (e.g. Th2), modulators of cytokines, chemokines or the receptors thereof (e.g. CCR5) or hormones (e.g., growth hormone) to ameliorate, combat, or eliminate infections as therapeutically appropriate.

CYP inhibitors can also be used as standalone therapeutics for CYP-mediated diseases, or as prophylactic agents for preventing the production of toxic metabolites. For example, an inhibitor of CYP2A6 or 2A13 can be used to ameliorate the carcinogenic effects of tobacco usage.

Such combination therapy in different formulations can be administered simultaneously, separately or sequentially. The CYP inhibitors can be administered prior to administration of the other drug to reduce CYP levels and minimize degradation of the drug. In specific embodiments, the CYP inhibitor is administered, 30 minutes, 1 hour, four hours, twelve hours or twenty four hours or more prior to initial administration of the other drug. The CYP inhibitors tend to have a long half life in vivo, presumably as a result of inhibiting their own metabolism. This means that once treatment has begun, the CYP inhibitor may be administered less frequently than the drug, although the skilled artisan will recognize that different administration regimens may be needed in specific situations. In certain instances, the CYP inhibitor may be administered for a period of time sufficient to reduce CYP levels in a subject sufficiently that a drug may be administered to the subject without additional dosing of the CYP inhibitor. Similarly, once CYP levels have been reduced, administration of the CYP inhibitor may not need to be carried out as frequently as administration of the drug. CYP inhibitors also can, in certain cases, induce expression of CYPs. The skilled artisan will appreciate that, in such cases, administration of the CYP inhibitor may need to be more frequent. Alternatively, such combinations can be administered as a single formulation, whereby the active ingredients are released from the formulation simultaneously or separately.

The following examples illustrate further the technology but, of course, should not be construed in any way of limiting its scope.

EXAMPLES

Example 1

Assay of $IC_{50}$ for CYP Inhibitors: Determinations Using Dibenzylfluorescein Metabolism by Human Liver Microsomes A microtiter plate based, fluorometric assay was used for the determination of the concentration of a test compound that will decrease by half the rate of metabolism by human liver microsomes of dibenzylfluorescein, a CYP3A4 substrate. The assay was run as described by Crespi et al. Anal. Biochem. 248:188-90 (1997).

Test compounds were diluted in acetonitrile in wells of a polypropylene micro-titer plate (Denville Scientific, Inc. Metuchen, N.J.). Three fold serial dilutions of the test article were made from the first well into the next seven wells of a row. Two wells of each row were used for positive controls containing no test compound and two for negatives containing 500 μM Ritonavir in acetonitrile. Test compounds in acetonitrile (0.004 mL) were added to wells of a micro-titer plate (Catalog No. 3598, Corning Costar, Cambridge, Mass.) containing a solution (0.096 mL) of 0.2 M $KPO_4$ buffer (pH 7.4) and an NADPH generating system (2.6 mM NADP, 6.6 mM glucose-6-phosphate, 3.3 mM $MgCl_2$ and 0.8 Units/mL G6P dehydrogenase (BD/Gentest, Woburn, Mass.). The plates were incubated for 10 minutes at 37° C. prior to addition of 0.1 mL of pre-warmed 0.1 mg/mL human liver microsomes (Xeno Tech, LLC, Lenexa, Kans.) in 0.2 M $KPO_4$ Buffer containing 2 μM dibenzylfluorescein (BD/Gentest, Woburn, Mass.). The plates were incubated for 10 minutes at 37° C. and the reaction are stopped by the addition of 0.075 mL of 2N NaOH. Plates were incubated at 37° C. for 1 hour prior to determining the amount of fluorescence in each well with a fluorescent plate reader (Spectra Max Gemini XS, Molecular Devices) at excitation/emission wavelengths of 485 and 538 nm (25 nm), respectively. Data were exported and analyzed using GraFit® (Erithacus Software Ltd., Surrey, U.K.). The background corrected data is fit to a 2-parameter equation for the determination of the $IC_{50}$.

Example 2

Preparation of Compound (2)

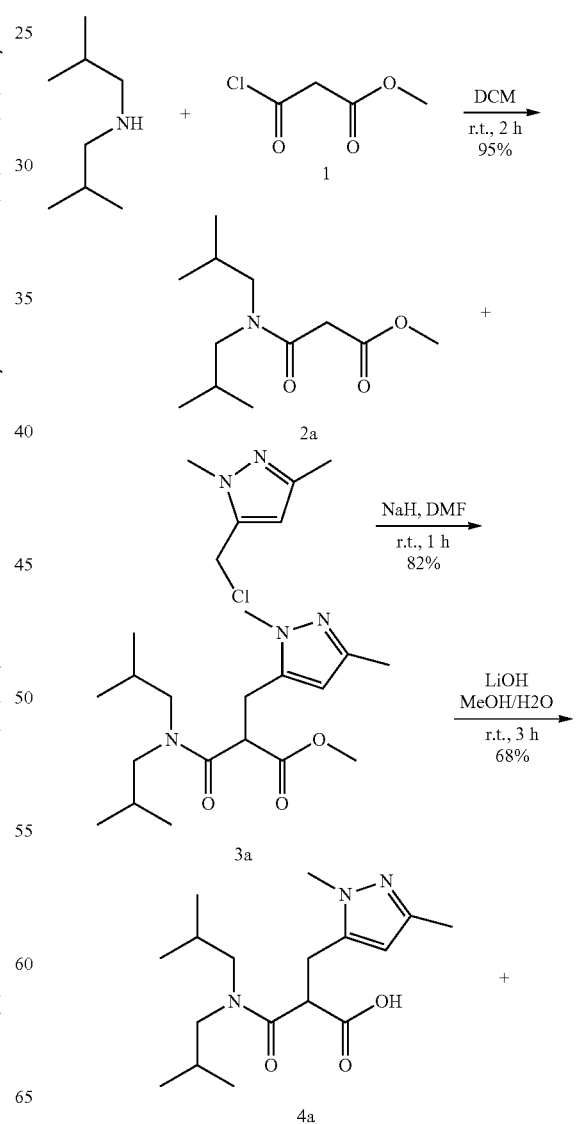

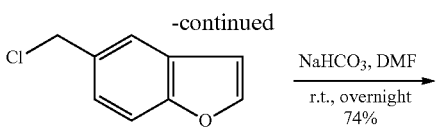

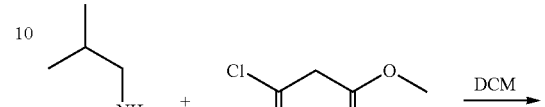

To a solution of methyl malonyl chloride 1 (10.0 g, 7.86 mL, 73.2 mmol, 1.0 equiv.) in dichloromethane (200 mL) at 0° C. was added rapidly dropwise a solution of diisobutylamine (23.7 g, 32 mL, 183 mmol, 2.5 equiv.) in dichloromethane (50 mL), and the reaction mixture was stirred at room temperature for 2 hours. Then the reaction mixture was diluted with additional dichloromethane (200 mL) and then washed successively with 1N HCl, saturated NaHCO$_3$ and brine. The organic phase was dried over Na$_2$SO$_4$, filtered and concentrated in vacuo. The residue was purified on silica gel by flash column chromatography with 1:1 ethyl acetate/hexane as eluant to afford the compound 2a as a light yellow oil (16 g, 95%). MS 481 (2MNa)$^+$, and 230 (MNa)$^+$. Purity>95% (HPLC).

A solution of 2a (1.58 g. 6.92 mmol, 1.0 equiv) in anhydrous DMF (7 mL) was treated with 60% sodium hydride (290 mg, 7.26 mmol, 1.05 equiv) at 0° C. After stiffing at this temperature for 5 min, 5-(chloromethyl)-1,3-dimethyl-1H-pyrazole (1.03 g, 6.92 mmol, 1.0 equiv, available from Maybridge) was introduced. Then the mixture was stirred at room temperature for 1 hour. The reaction was quenched with saturated aqueous NaCl Solution. The resulting solution was extracted with ethyl acetate (40 mL×3). The combined organic extracts were washed once with brine, dried over Na$_2$SO$_4$, filtered and concentrated in vacuo. The residue was chromatographed on silica gel with ethyl acetate/hexane as eluant to afford the compound 3a as a light yellow oil (1.91 g, 82%). MS 338 (MH)$^+$, and 336 (M-H)$^-$. Purity 95% (HPLC).

To a solution of 3a (1.84 g, 5.45 mmol, 1.0 equiv) in MeOH (24 mL) was added 1N aqueous LiOH (6 mL, 6.01 mmol, 1.1 equiv), and the reaction mixture was stirred at room temperature for 3 hours. The mixture was concentrated in vacuo to remove most of the MeOH and then diluted with water. The resulting solution was extracted with hexane (3×), and the pH of the aqueous phase was adjusted to 3 with concentrated HCl, and then it was extracted with ethyl acetate (3×). The combined ethyl acetate extracts were washed once with brine, dried over anhydrous Na$_2$SO$_4$ and concentrated in vacuo to afford the crude target as a white solid. Recrystallization from hexane/ether afforded a pure sample of 4a (1.19 g, 68%) as a white solid. MS 324 (MH)$^+$, and 278 (M-COOH)$^-$. Purity 95% (HPLC).

To a suspension of 4a (74 mg, 0.23 mmol, 1.0 equiv.) and sodium hydrogen carbonate (38 mg, 0.46 mmol, 2.0 equiv.) in DMF (2.4 mL), 5-chloromethylbenzofuran (84 mg, 0.50 mmol, 2.2 equiv.) (prepared by the reaction of benzofuran-5-yl-methanol with thionyl chloride in dichloromethane), was added at room temperature. The mixture was allowed to react for 24 hours, then brine was added and the product extracted with ethyl acetate. The combined organic phase was washed with brine, dried over Na$_2$SO$_4$, and concentrated in vacuo. The residue was purified by prep-TLC (EA/Hex 1/1) to give compound 2 (77 mg, 74%) as a oil. MS 454 (MH)$^+$, and 452 (M-H)$^-$. Purity 98% (HPLC).

Example 3

Preparation of Compound (9)

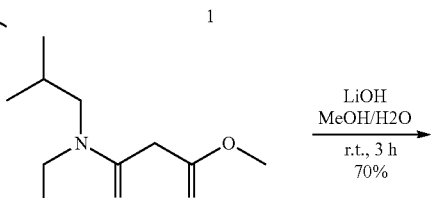

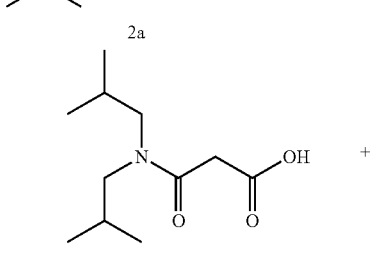

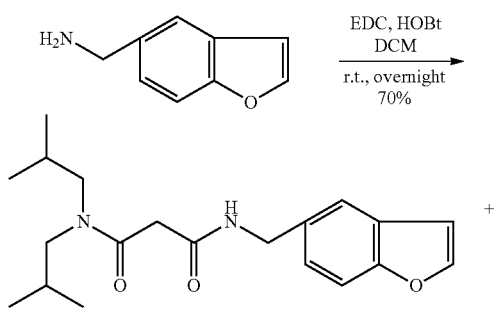

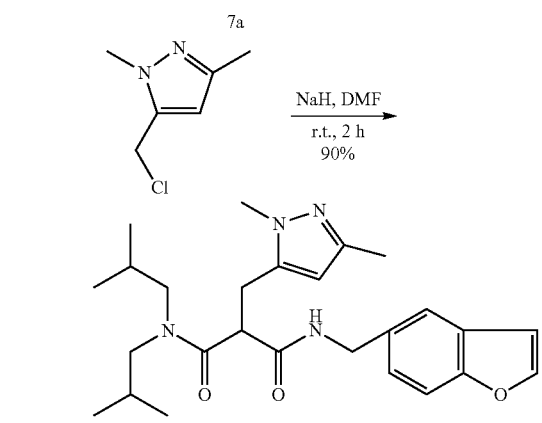

To a solution of 2a (36.4 g, 159 mmol, 1.0 equiv) in MeOH (699 mL) was added 1N aqueous LiOH (175 mL, 175 mmol, 1.1 equiv), and the reaction mixture was stirred at room temperature for 3 hours. Then the mixture was concentrated to remove most of the MeOH and diluted with water (480 mL). The aqueous solution was extracted with hexane (300 mL×3), the pH was adjusted to 3 with concentrated HCl, and then it was extracted with ether (500 mL×3). The combined ether extracts were washed once with brine, dried over anhydrous Na$_2$SO$_4$ and concentrated in vacuo to afford the crude product as a white solid, which contains a small amount of starting material. Recrystallization from hexane afforded 6a (24 g, 70%) as a white solid, mp 72.1-72.6° C. MS 453 (2MNa)$^+$, 216 (MH)$^+$, and 214 (M-H)$^-$. Purity>99% (HPLC).

(5-Benzofuran-yl)methylamine (7.0 g, 46 mmol, 1.0 equiv) and 6a (10.9 g, 51 mmol, 1.1 equiv) were dissolved in dichloromethane (460 mL). To the solution were added HOBt (6.23 g, 46 mmol, 1.0 equiv) and EDC.HCl (9.73 g, 51 mmol, 1.1 equiv) at 0° C. Then the mixture was stirred at room temperature overnight. The reaction was quenched with 10% ammonium hydroxide solution (200 mL). The two layers were separated and the organic phase was washed successively with 1N HCl, saturated NaHCO$_3$ and brine. The final organic solution was dried over MgSO$_4$, filtered, and concentrated in vacuo to afford the crude product. It solidified in the freezer. Recrystallization from ethyl acetate/hexane (20/80) afforded 7a (11 g, 70%) as a white solid, mp 66.5-67.1° C. MS 345 (MH)$^+$, 403 (MOAc)$^-$, 381 (MCl$^{37}$)$^-$, 379 (MCl$^{35}$)$^-$ and 343 (M-H)$^-$. Purity>99% (HPLC).

A solution of 7a (10.4 g. 30.2 mmol, 1.0 equiv) in anhydrous DMF (100 mL) was treated with 60% sodium hydride (1.45 g, 36.2 mmol, 1.2 equiv) at 0° C. After stirring at this temperature for 15 min, a solution of 5-(chloromethyl)-1,3-dimethyl-1H-pyrazole (4.95 g, 33.2 mmol, 1.1 equiv) in DMF (30 mL) was introduced. Then the mixture was stirred at room temperature for 2 hours. The reaction was quenched with saturated NaHCO$_3$ (200 mL) followed by water (200 mL). The resulting solution was extracted with ether (250 mL×3). The combined ether extracts were washed twice with brine, dried over Na$_2$SO$_4$, filtered and concentrated in vacuo. The residue was chromatographed on silica gel with ether/dichloromethane/methanol (50/50/1) to afford the target as an oil (12.3 g, 90%). Trituration with ether/hexane (1:2) afforded compound 9 (10.1 g) as a white solid, mp 85.5-86.0° C. The filtrate was concentrated and triturated to give an additional 1.76 g of the target compound. MS 453 (MH)$^+$, 511 (MOAc)$^-$, 489 (MCl$^{37}$)$^-$, 487 (MCl$^{35}$)$^-$ and 451 (M-H)$^-$. Purity>99% (HPLC).

Example 4

Preparation of Compound (11)

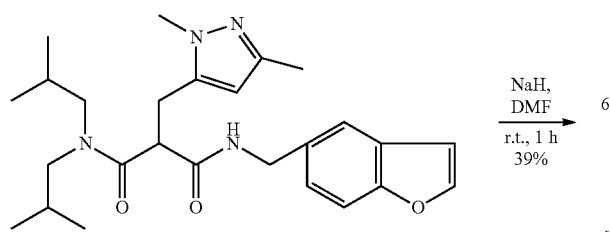

9

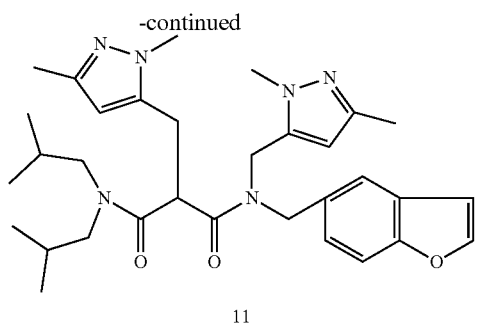

11

A solution of compound 9 (56 mg, 0.12 mmol, 1.0 equiv) in anhydrous DMF (0.2 mL) was treated with 60% sodium hydride (6.0 mg, 0.15 mmol, 1.2 equiv) at room temperature. After stirring at this temperature for 5 min, 5-(chloromethyl)-1,3-dimethyl-1H-pyrazole (21 mg, 0.14 mmol, 1.1 equiv) was introduced. Then the mixture was stirred at room temperature for 1 hour. The reaction was quenched with saturated aqueous NaHCO$_3$ solution. The resultant solution was extracted with ethyl acetate. The combined organic extracts were washed once with brine, dried over Na$_2$SO$_4$, filtered and concentrated in vacuo. The residue was chromatographed on prep-TLC (ethyl acetate/dichloromethane/methanol 20:20:1, 2 runs) to afford compound 11 (27 mg, 39%) as an oil. MS 561 (MH)$^+$, 619 (MOAc)$^-$, 597 (MCl$^{37}$)$^-$, 595 (MCl$^{35}$)$^-$ and 559 (M-H)$^-$. Purity>98% (HPLC).

Example 5

Preparation of Compound (27)

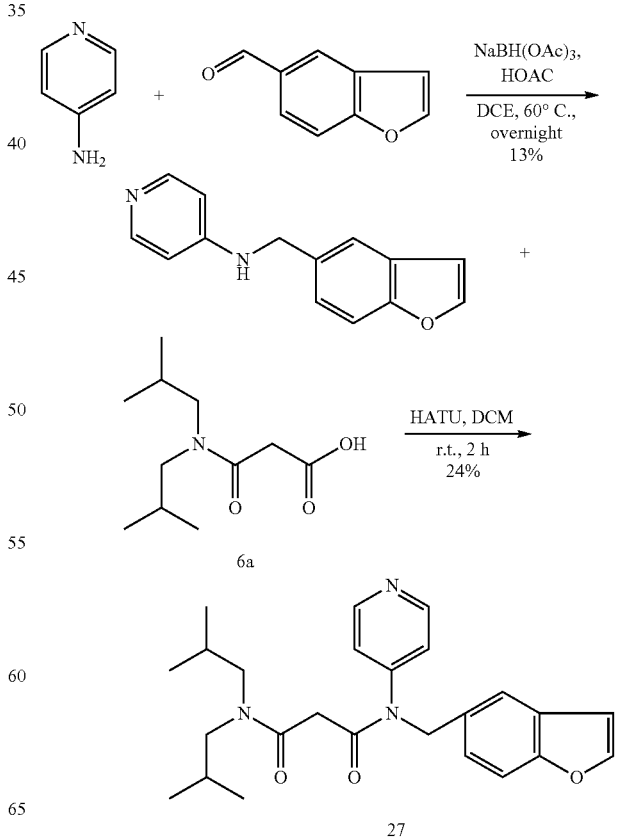

27

Benzofuran-5-carbaldehyde (330 mg, 2.19 mmol, 1.0 equiv.) and 4-aminopyridine (227 mg, 2.41 mmol, 1.1 equiv.) were combined in 1,2-dichloroethane (22 mL) and treated with acetic acid (138 μl, 2.41 mmol, 1.1 equiv.) and sodium triacetoxyborohydride (969 mg, 4.34 mmol, 1.98 equiv.). The mixture was stirred at 60° C. overnight, and then quenched by addition of saturated NaHCO$_3$ solution. The two phases were separated and the water layer was extracted twice with ethyl acetate. The combined organic extract was dried over Na$_2$SO$_4$, filtered and concentrated in vacuo. The residue was purified with flash column chromatography on silica gel, eluting with ethyl acetate/dichloromethane/methanol to afford N-(benzofuran-5-ylmethyl) pyridin-4-amine as a white solid (62 mg, 13% yield). Mass: 225 (MH)$^+$. Purity>99% (HPLC).

N-(benzofuran-5-ylmethyl)pyridin-4-amine (20 mg, 0.10 mmol, 1.0 equiv) and 6a (22 mg, 0.10 mmol, 1.0 equiv) were dissolved in dichloromethane (1 mL). To the solution were added HATU (57 mg, 0.15 mmol, 1.5 equiv) and DIPEA (52 μL, 0.3 mmol, 3.0 equiv) at 0° C. Then the mixture was stirred at room temperature for 2 hours. Then the reaction solution was transferred onto a prep-TLC plate with a syringe. The plate was run in the solvent system (dichloromethane/ethyl acetate/methanol 100/50/1, 2 runs) to give compound 27 (10 mg, 24%) as an oil. MS 422 (MH)$^+$. Purity>99% (HPLC).

Example 6

Preparation of Compound (3)

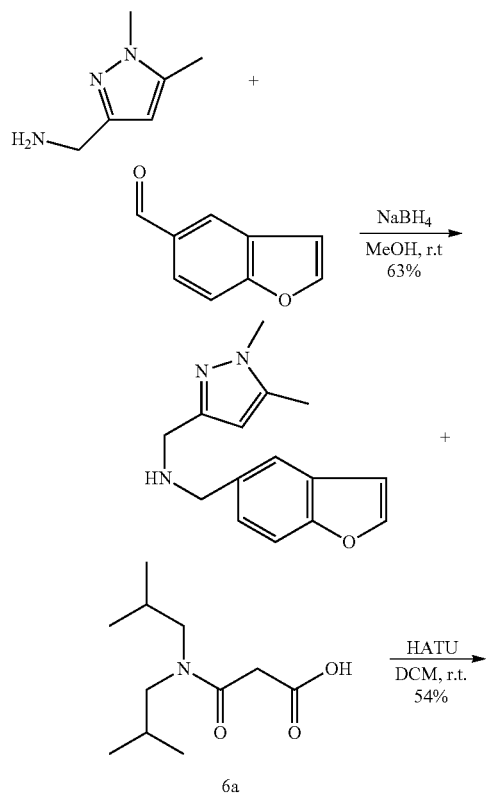

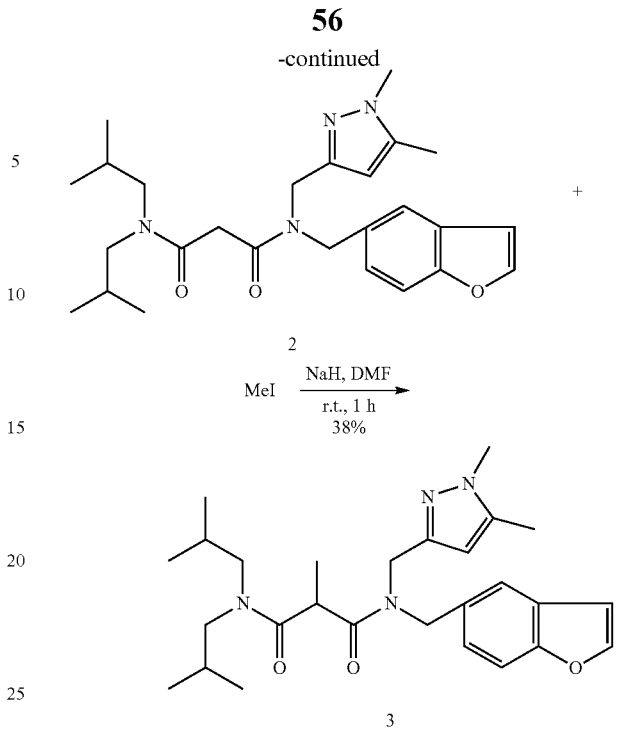

To a solution of benzofuran-5-carbaldehyde (526 mg, 3.6 mmol, 1.2 equiv) in MeOH (15 mL) were added NaOAc (246 mg, 3.0 mmol, 1.0 equiv), HOAc (172 μL, 3.0 mmol, 1.0 equiv) and (1,5-dimethyl-1-pyrazole-3-yl)methylamine (376 mg, 3.0 mmol, 1.0 equiv., available from Maybridge). The mixture was stirred at room temperature for 5 min, and then treated with NaBH$_4$ (273 mg, 7.2 mmol, 2.4 equiv) at 0° C. The resulting mixture was allowed to return to room temperature and stirred for 1 h, after which time the reaction was quenched with 1N NaOH. The mixture was concentrated in vacuo to remove most of the MeOH, and the water layer was extracted with ethyl acetate three times. The combined organic phase was dried over Na$_2$SO$_4$, filtered and concentrated in vacuo. The residue was purified on silica gel with ethyl acetate/dichloromethane/methanol 5/5/1 as eluant to afford 1-(Benzofuran-5-yl)-N-((1,5-dimethyl-1H-pyrazol-3-yl)methyl)methanamine (478 mg, 63%). MS 256 (MH)$^+$. Purity 95% (HPLC).

1-(Benzofuran-5-yl)-N-((1,5-dimethyl-1H-pyrazol-3-yl) methyl)methanamine (350 mg, 1.37 mmol, 1.0 equiv), and 6a (310 mg, 1.44 mmol, 1.05 equiv) were dissolved in dichloromethane (10 mL). To the solution were added HATU (574 mg, 1.51 mmol, 1.1 equiv) and DIPEA (0.70 mL, 4.11 mmol, 3.0 equiv) at 0° C. Then the mixture was stirred at room temperature for 3 hours. The reaction was quenched with saturated aqueous NH$_4$Cl followed by dichloromethane. The layers were separated and the organic phase was washed twice with aqueous NH$_4$Cl, dried over Na$_2$SO$_4$, filtered, and concentrated in vacuo. The residue was chromatographed on silica gel with ethyl acetate/dichloromethane/methanol as eluent to afford compound 2 (332 mg, 54%) as an oil. MS 453 (MH)$^+$. Purity>99% (HPLC).

A solution of 2 (223 mg. 0.49 mmol, 1.0 equiv) in anhydrous DMF (1.0 mL) was treated with 60% sodium hydride (22 mg, 0.54 mmol, 1.1 equiv) at room temperature. After stiffing at this temperature for 5 min, iodomethane (46 μL, 0.74 mmol, 1.5 equiv) in DMF (1 mL) was introduced. Then the mixture was stirred at room temperature for 1 hour.

The reaction was quenched with saturated aqueous NaHCO$_3$. The resulting solution was extracted with ethyl acetate. The combined organic extracts were washed once with brine, dried over Na$_2$SO$_4$, filtered and concentrated in vacuo. The residue was recrystallized from ethyl acetate/hexane at 0° C. to give compound 3 (88 mg, 38%) as a low melting solid MS 489 (MNa)$^+$, and 467 (MH)$^+$. Purity 98% (HPLC).

Example 7

Preparation of Compounds (17) and (18)

was introduced. Then the mixture was heated to 60° C. and stirred for 1 hour. The reaction was quenched with saturated aqueous NaHCO$_3$. The resulting solution was extracted with ethyl acetate. The combined organic extracts were washed once with brine, dried over Na$_2$SO$_4$, filtered and concentrated in vacuo. The residue was chromatographed on silica gel with ethyl acetate/hexane as eluent to give compound 17 (31 mg, 29%) as a white solid. MS 653 (MNa)$^+$, 631 (MH)$^+$ and 629 (M-H)$^-$. Purity 96% (HPLC). Continued elution provided compound 18 (23 mg, 15%) as a white solid. MS

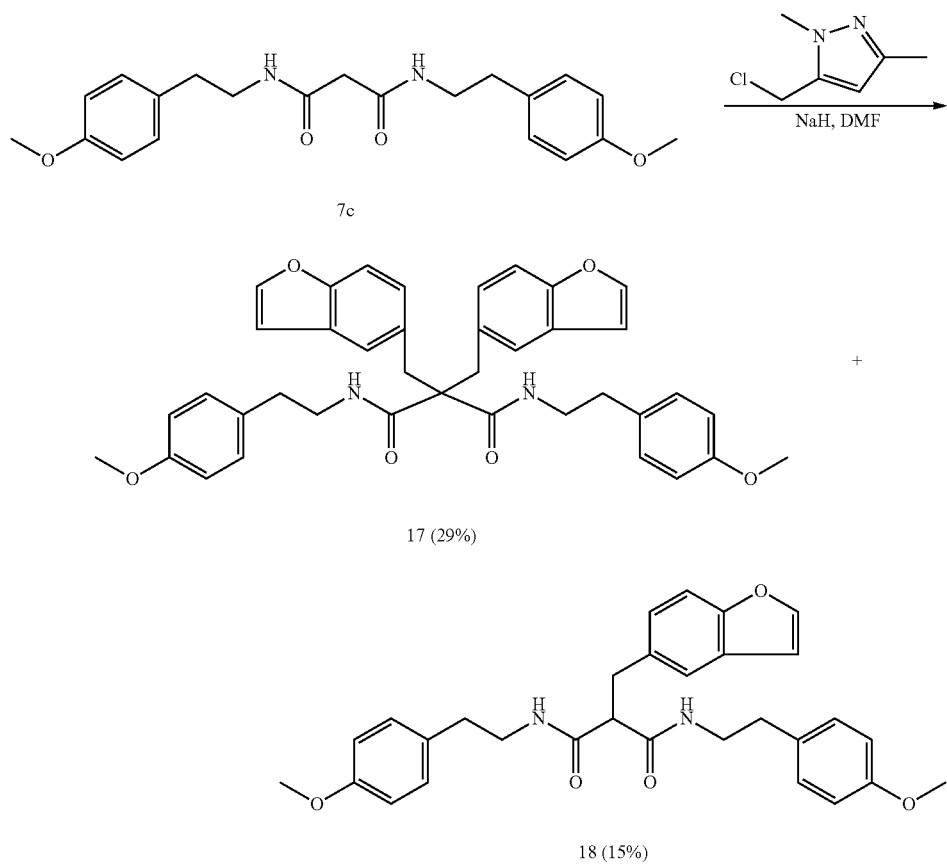

A solution of N,N-bis[2-(4-methoxyphenyl)ethyl]propanediamide 7b (126 mg. 0.34 mmol, 1.0 equiv., available from UkrOrg Synthesis Ltd.) in anhydrous DMF (1.7 mL) was treated with 60% sodium hydride (17 mg, 0.41 mmol, 1.2 equiv) at room temperature. After stiffing for 5 min, 5-chloromethylbenzofuran (50 µL, 0.37 mmol, 1.1 equiv)

501 (MH)$^+$, 559 (MOAc)$^-$, 535 (MCl$^{35}$)$^-$. Purity>99% (HPLC).

Example 8

Preparation of Compound (28)

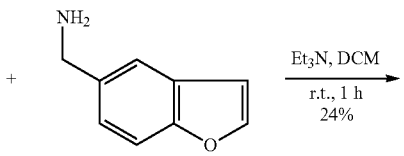

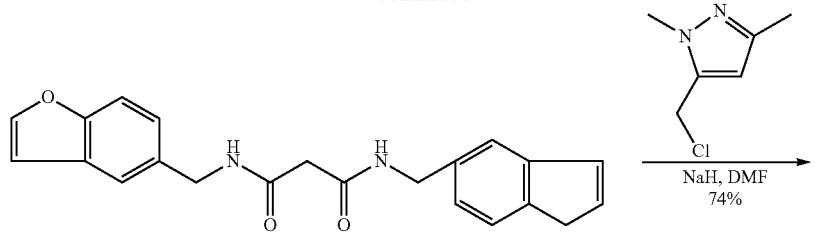

7c

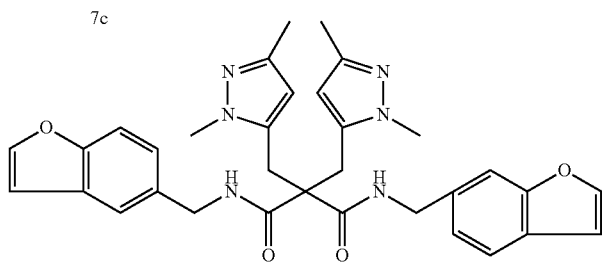

28

To a solution of 1-benzofuran-5-ylmethylamine (589 mg, 4.0 mmol, 2.0 equiv) and triethylamine (585 μL, 4.2 mmol, 2.1 equiv) in dichloromethane (10 mL) was slowly added a solution of malonyl dichloride (195 μL, 2.0 mmol, 1.0 equiv) in dichloromethane (10 mL) at 0° C. After the addition, the solution was allowed to return to room temperature and stirred for 1 hour. The reaction was quenched with 1.0 M HCl followed by dichloromethane. The separated aqueous layer was extracted with dichloromethane twice. The combined dichloromethane layers were washed once with brine, dried over $Na_2SO_4$, and concentrated in vacuo. The residue was chromatographed on silica gel with ethyl acetate and dichloromethane as eluent to give N,N-bis(benzofuran-5-ylmethyl)malonamide 7c (175 mg, 24%) as a light yellow solid.

A solution of N,N-bis(benzofuran-5-ylmethyl)malonamide 7c (73 mg, 0.20 mmol, 1.0 equiv) in anhydrous DMF (1.0 mL) was treated with 60% sodium hydride (18 mg, 0.44 mmol, 2.2 equiv) at room temperature. After stiffing for 5 min, 5-(chloromethyl)-1,3-dimethyl-1H-pyrazole (63 mg, 0.42 mmol, 2.1 equiv) was introduced. Then the mixture was stirred at room temperature for 2 hours. The reaction was quenched with saturated aqueous $NaHCO_3$. The resulting solution was extracted with ethyl acetate. The combined organic extracts were washed once with brine, dried over $Na_2SO_4$, filtered and concentrated in vacuo. The residue was chromatographed on silica gel with ethyl acetate/dichloromethane/methanol as eluent to give compound 28 (86 mg, 74%) as an oil. MS 579 $(MH)^+$, 615 $(MCl^{37})^-$, 613 $(MCl^{35})^-$ and 577 $(M-H)^-$. Purity 99% (HPLC).

Example 9

Preparation of Compound (29)

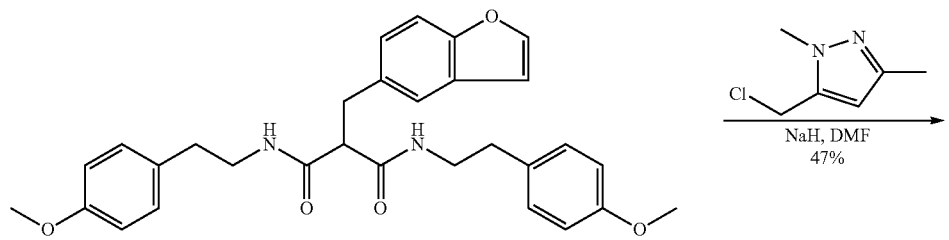

18

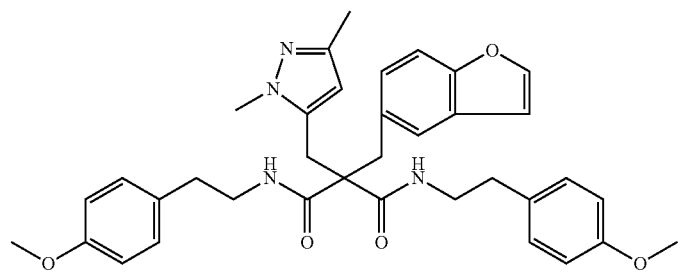

29

A solution of 18 (100 mg, 0.20 mmol, 1.0 equiv) in anhydrous DMF (0.60 mL) was treated with 60% sodium hydride (9.0 mg, 0.22 mmol, 1.1 equiv) at room temperature. After stirring for 5 min, 5-(chloromethyl)-1,3-dimethyl-1H-pyrazole (32 mg, 0.22 mmol, 1.1 equiv) was introduced. Then the mixture was stirred at room temperature for 1 hour. The reaction was quenched with saturated aqueous NaHCO$_3$. The resulting solution was extracted with ethyl acetate. The combined organic extracts were washed once with brine, dried over Na$_2$SO$_4$, filtered and concentrated in vacuo. The residue was purified by prep-TLC (ethyl acetate/dichloromethane 1/1) to afford compound 29 as a white solid (57 mg, 47%). MS 609 (MH)$^+$, 645 (MCl$^{37}$)$^-$, 643 (MCl$^{35}$)$^-$ and 607(M-H)$^-$. Purity 99% (HPLC).

Example 10

Preparation of Compound (30)

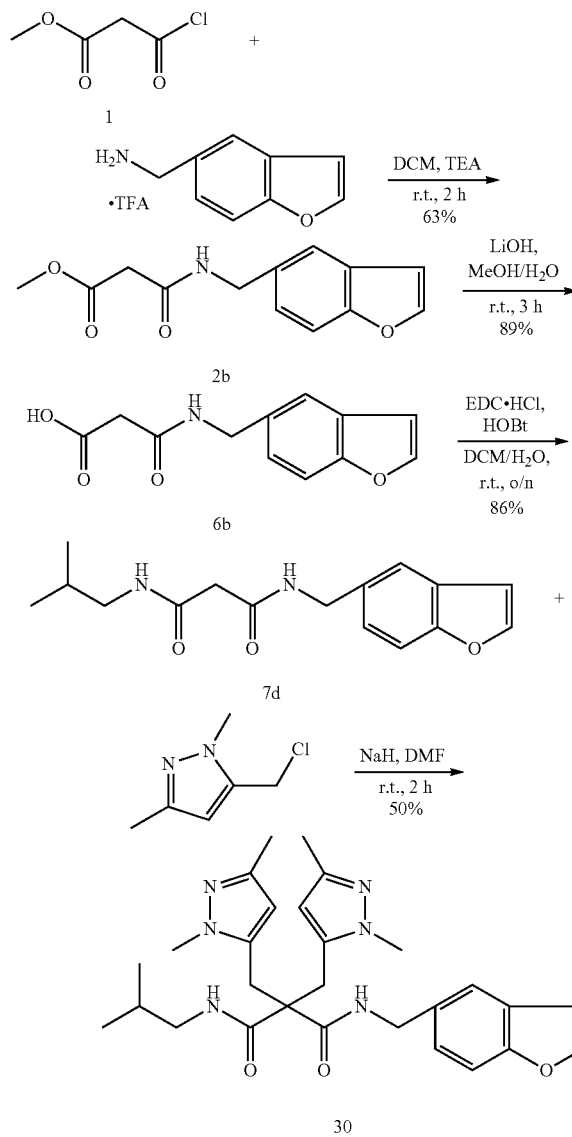

To a solution of methyl malonyl chloride 1 (555 μL, 5.0 mmol, 1.0 equiv.) in dichloromethane (15 mL) at 0° C. was added dropwise a solution of 5-aminomethylbenzofuran-TFA (1.3 g, 5.0 mmol, 1.0 equiv.) and triethylamine (1.5 mL, 10.5 mmol, 2.1 equiv.) in dichloromethane (5 mL), and the reaction mixture was stirred at room temperature for 2 hours. It was diluted with additional dichloromethane (20 mL) and then washed successively with 1N HCl, saturated NaHCO$_3$ and brine. The organic phase was dried over Na$_2$SO$_4$, filtered and concentrated in vacuo. The residue was recrystallized from ethyl acetate/hexane to give compound 2b as a white solid (364 mg). The filtrate was concentrated and chromatographed on silica gel with ethyl acetate/hexane as eluent to give an additional 408 mg of compound 2b (total yield 63%). MS 248 (MH)$^+$, and 246 (M-H)$^-$. Purity 99% (HPLC).

To a solution of 2b (741 mg, 3.0 mmol, 1.0 equiv) in MeOH (13.2 mL) was added 1N aqueous LiOH (3.3 mL, 3.3 mmol, 1.1 equiv), and the reaction mixture was stirred at room temperature for 3 hours. The mixture was concentrated to remove most of the MeOH and then was diluted with water. The solution's pH was adjusted to 3 with concentrated HCl, and it was then extracted with ethyl acetate (30 mL×3). The combined organic extracts were washed once with brine, dried over anhydrous Na$_2$SO$_4$ and concentrated in vacuo to afford a white solid. Recrystallization from ethyl acetate provided compound 6b (620 mg, 89%) as a white solid. MS 234 (MH)$^+$, 232 (M-H)$^-$. Purity>99% (HPLC).

Isobutylamine (110 μL, 1.1 mmol, 1.1 equiv) and 6b (233 mg, 1.0 mmol, 1.0 equiv) were dissolved in dichloromethane (5 mL) and water (5 mL). To the solution were added HOBt (135 mg, 1.0 mmol, 1.0 equiv) and EDC.HCl (211 mg, 1.1 mmol, 1.1 equiv) at 0° C. Then the mixture was stirred at room temperature overnight. Since the reaction had not gone to completion, the same amounts of isobutylamine, HOBT and EDC were added and the mixture was stirred at room temperature for 4 h. Complete conversion was observed. The solution was diluted with dichloromethane. The separated organic phase was washed successively with 1N HCl, saturated NaHCO$_3$ and brine. The organic extracts were dried over MgSO$_4$, filtered, and concentrated in vacuo. Recrystallization of the residue from ethyl acetate/hexane (1/4) gave compound 7d (248 mg, 86%) as a white solid. MS 289 (MH)$^+$, 347 (MOAc)$^-$, and 287 (M-H)$^-$. Purity>99% (HPLC).

A solution of 7d (58 mg, 0.20 mmol, 1.0 equiv) in anhydrous DMF (0.8 mL) was treated with 60% sodium hydride (18 mg, 0.44 mmol, 2.2 equiv). After stiffing at room temperature for 5 min, 5-(chloromethyl)-1,3-dimethyl-1H-pyrazole (63 mg, 0.42 mmol, 2.1 equiv) was introduced. Then the mixture was stirred at room temperature for 2 hours. The reaction was quenched with saturated aqueous NaHCO$_3$. The resulting solution was extracted with ethyl acetate. The combined extracts were washed once with brine, dried over Na$_2$SO$_4$, filtered and concentrated in vacuo. The residue was purified by prep-TLC (ethyl acetate/dichloromethane/methanol 10/10/1, 2 runs) to afford compound 30 (50 mg, 50%) as a white solid. MS 505 (MH)$^+$, 503 (M-H)$^-$. Purity 99% (HPLC).

Example 11

Preparation of Compound (1)

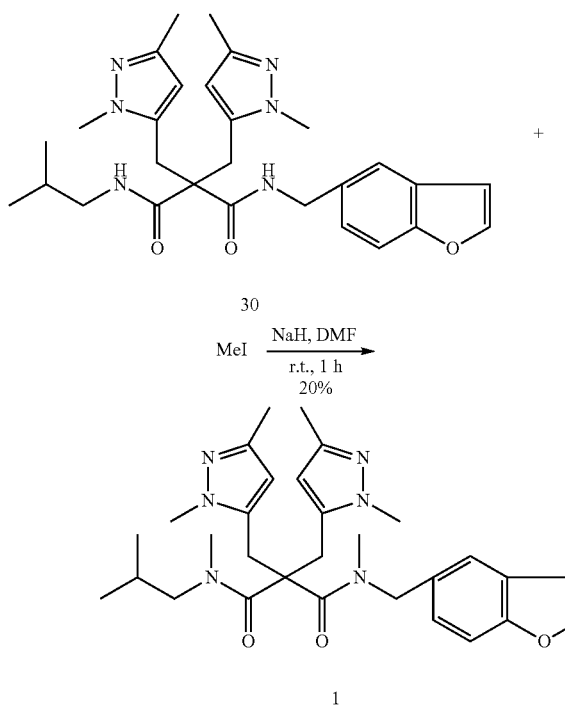

A solution of 30 (101 mg, 0.20 mmol, 1.0 equiv) in anhydrous DMF (1.0 mL) was treated with 60% sodium hydride (18 mg, 0.44 mmol, 2.2 equiv). After stirring at room temperature for 5 min, iodomethane (63 μL, 1.0 mmol, 5.0 equiv) was introduced. Then the mixture was stirred at room temperature for 1 hour. The reaction was quenched with saturated aqueous $NaHCO_3$. The resulting solution was extracted with ethyl acetate. The combined extracts were washed once with brine, dried over $Na_2SO_4$, filtered and concentrated in vacuo. The residue was purified by prep-TLC (ethyl acetate/dichloromethane/methanol 10/10/1, 2 runs) to afford a mixture of monomethylated and dimethylated compounds. The mixture was repurified using reverse phase prep-HPLC to give the compound 1 (21 mg, 20%) as a white solid. MS 533 (MH)$^+$. Purity 99% (HPLC).

Variations, modifications, and other implementations of what is described herein will occur to those of ordinary skill in the art without departing from the spirit and the scope of the technology. Accordingly, the technology is not to be limited only to the preceding illustrative descriptions.

What is claimed is:

1. A method of inhibiting cytochrome P450 monooxygenase in a subject, comprising administering to said subject in need thereof an effective amount of a compound having the formula:

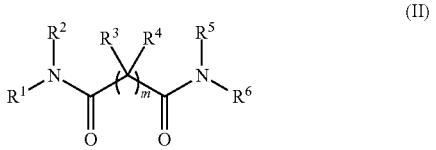

(II)

wherein:
m is 1-3;
at least one of $R^1$, $R^2$, $R^3$, $R^4$, $R^5$, and $R^6$ is $C_1$-$C_6$ alkyl substituted with an otherwise unsubstituted benzofuran, wherein said alkyl is linked to the 4, 5, 6, or 7 position of the benzofuran;
each $R^1$, $R^2$, $R^3$, $R^4$, $R^5$, and $R^6$ independently is selected from the group consisting of H, optionally substituted $C_1$-$C_8$ alkyl, optionally $C_3$-$C_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl;
where each optional substituent is independently selected from the group consisting of halo, —CN, —$NO_2$, —$CO_nR$, —$CON(R)_2$, —C(S)R, —$C(S)N(R)_2$, —$SO_nN(R)_2$, —SR, —$SO_nR$, —$N(R)_2$, —$N(R)CO_nR$, —$NRS(O)_nR$, —NRC[=N(R)]$N(R)_2$, —N(R)N(R)$CO_nR$, —$NRPO_nN(R)_2$, —$NRPO_nOR$, oxo, =N—OR, =N—$N(R)_2$, =NR, =$NNRC(O)N(R)_2$, =$NNRCO_nR$, =$NNRS(O)_nN(R)_2$, =$NNRS(O)_n(R)$ $C_1$-$C_8$ alkyl, OR, $C_1$-$C_8$ alkyl, $C_2$—$C_6$ alkenyl, $C_2$-$C_6$ alkynyl, $C_3$-$C_8$ cycloalkyl, $C_5$-$C_8$ cycloalkenyl, heterocyclo, aryl, and heteroaryl;
each R is independently selected from the group consisting of: H, $C_1$-$C_8$ alkyl, $C_3$-$C_8$ cycloalkyl, cycloalkylalk, aryl, aralkyl, heteroaryl, heteroaralkyl, heterocyclo, heterocycloalkyl, and heterocycloalkylalkyl; and
each n is independently 1 or 2;
or a stereoisomeric form or pharmacologically acceptable salt thereof;
provided that at least two of $R^1$, $R^2$, $R^3$, $R^4$, $R^5$, and $R^6$ are not H; and
provided that when $R^1$ and $R^2$ are isobutyl, $R^3$ and $R^4$ are H, and $R^5$ is $CH_2$-[5]-benzofuranyl, then $R^6$ cannot be —$CH_2$-4-pyridyl, —$CH_2$-1,5-dimethyl-3-pyrazolyl, or —CH2-4-methyl-2-thiazolyl.

2. The method according to claim 1, wherein said subject is a patient is suffering from chronic pain, depression, epilepsy, psychosis, inflammation, cancer, cardiovascular disease, diabetes, neurodegenerative disease, and/or infection.

3. The method according to claim 2, wherein the patient is suffering from HCV or HIV infection.

4. The method according to claim 1, wherein the compound is administered prior to, and/or substantially contemporaneously with, a drug wherein efficacy of said drug is compromised due to degradation by cytochrome P450 monooxygenase.

5. A method of reducing toxicity in a subject of a compound that is metabolized by cytochrome P450 monooxygenase to a toxic metabolite, comprising administering to said subject in need thereof an effective amount of a compound having the formula:

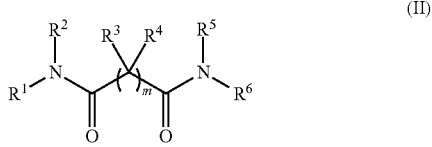

(II)

wherein:
m is 1-3;
at least one of $R^1$, $R^2$, $R^3$, $R^4$, $R^5$, and $R^6$ is $C_1$-$C_6$ alkyl substituted with an otherwise unsubstituted benzofuran, wherein said alkyl is linked to the 4, 5, 6, or 7 position of the benzofuran;
each $R^1$, $R^2$, $R^3$, $R^4$, $R^5$, and $R^6$ independently is selected from the group consisting of H optionally substituted $C_1$-$C_8$ alkyl, optionally substituted $C_3$-$C_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl;
where each optional substituent is independently selected from the group consisting of halo, —CN, —NO$_2$, —CO$_n$R, —CON(R)$_2$, —C(S)R, —C(S)N(R)$_2$, —SO$_n$N(R)$_2$, —SR, —SO$_n$R, —N(R)$_2$, —N(R)CO$_n$R, —NRS(O)$_n$R, —NRC[=N(R)]N(R)$_2$, —N(R)N(R) CO$_n$R, —NRPO$_n$N(R)$_2$, —NRPO$_n$OR, oxo, =N—OR, =N—N(R)$_2$, =NR, =NNRC(O)N(R)$_2$, =NNRCO$_n$R, =NNRS(O)$_n$N(R)$_2$, =NNRS(O)$_n$(R) $C_1$-$C_8$ alkyl, OR, $C_1$-$C_8$ alkyl, $C_2$—$C_6$ alkenyl, $C_2$-$C_6$ alkynyl, $C_3$-$C_8$ cycloalkyl, $C_5$-$C_8$ cycloalkenyl, heterocyclo, aryl, and heteroaryl;
each R is independently selected from the group consisting of: H, $C_1$-$C_8$ alkyl, $C_3$-$C_8$ cycloalkyl, cycloalkylalk, aryl, aralkyl, heteroaryl, heteroaralkyl, heterocyclo, heterocycloalkyl, and heterocycloalkylalkyl; and
each n is independently 1 or 2;
or a stereoisomeric form or pharmacologically acceptable salt thereof;
provided that at least two of $R^1$, $R^2$, $R^3$, $R^4$, $R^5$, and $R^6$ are not H; and
provided that when $R^1$ and $R^2$ are isobutyl, $R^3$ and $R^4$ are H, and $R^5$ is CH$_2$-[5]-benzofuranyl, then $R^6$ cannot be —CH$_2$-4-pyridyl, —CH$_2$-1,5-dimethyl-3-pyrazolyl, or —CH2-4-methyl-2-thiazolyl.

6. The method according to claim 1, wherein $R^3$ is H and $R^4$ is selected from the group consisting of H, optionally substituted $C_1$-$C_8$ alkyl, optionally substituted $C_3$-$C_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl.

7. The method according to claim 1, wherein $R^1$ is optionally substituted $C_1$-$C_8$ alkyl.

8. The method according to claim 7, wherein $R^2$ is optionally substituted $C_1$-$C_8$ alkyl.

9. The method according to claim 1, wherein $R^4$ is optionally substituted $C_1$-$C_8$ alkyl or optionally substituted heteroaralkyl.

10. The method according to claim 1, wherein $R^6$ is H, optionally substituted $C_1$-$C_8$ alkyl or optionally substituted heteroaralkyl.

11. The method according to claim 8, wherein $R^3$ is H, $R^4$ is H, optionally substituted $C_1$-$C_8$ alkyl or optionally substituted heteroaralkyl and $R^6$ is H, optionally substituted $C_1$-$C_8$ alkyl or optionally substituted heteroaralkyl.

12. The method according to claim 1 wherein $R^3$ is $C_1$-$C_6$ alkyl substituted with an otherwise unsubstituted benzofuran, wherein said alkyl is linked to the 4, 5, 6, or 7 position of the benzofuran.

13. The method according to claim 12, wherein $R^4$ is H or $C_1$-$C_8$ alkyl.

14. The method according to claim 12, wherein $R^4$ is H and $R^5$ is H.

15. The method according to claim 14, wherein $R^6$ is selected from the group consisting of optionally substituted $C_1$-$C_8$ alkyl, optionally substituted $C_3$-$C_8$ cycloalkyl, optionally substituted cycloalkylalkyl, optionally substituted aryl, optionally substituted aralkyl, optionally substituted heteroaryl, optionally substituted heteroaralkyl, optionally substituted heterocyclo, optionally substituted heterocycloalkyl, and optionally substituted heterocycloalkylalkyl.

16. The method according to claim 1 wherein $R^1$ is $C_1$-$C_6$ alkyl substituted with an otherwise unsubstituted benzofuran, wherein said alkyl is linked to the 4, 5, 6, or 7 position of the benzofuran.

17. The method according to claim 16, wherein $R^3$ and $R^4$ are each independently heteroaralkyl.

18. The method according to claim 16, wherein $R^3$ and $R^4$ are each independently heteroarylmethyl.

19. The method according to claim 1, wherein said compound is selected from the group consisting of

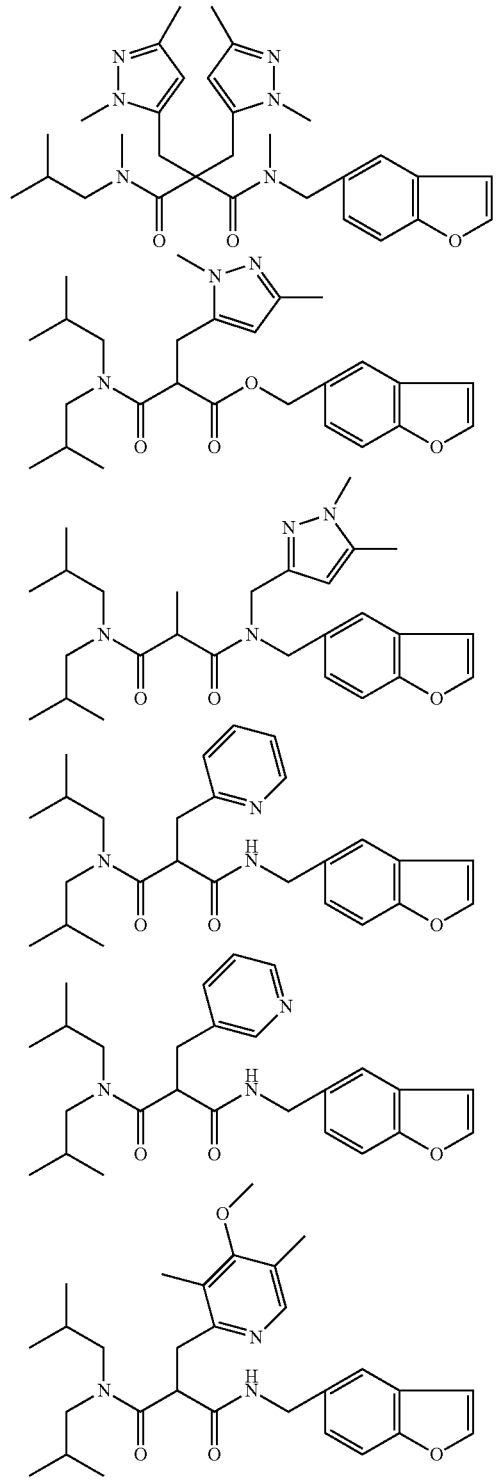

67
-continued
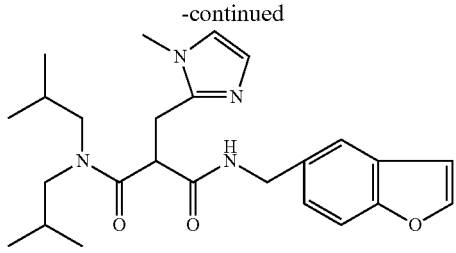
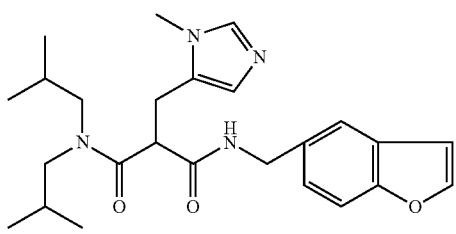
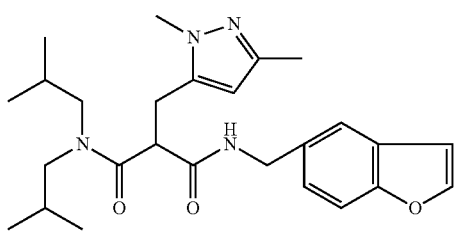
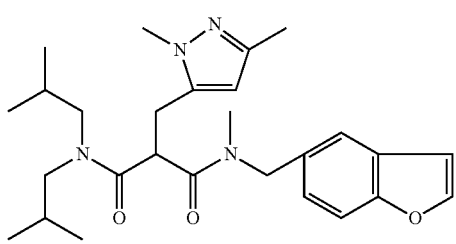
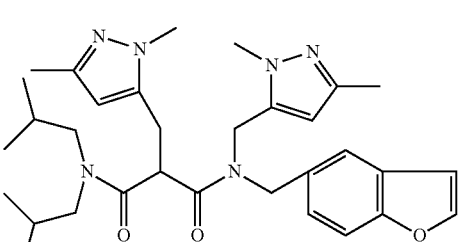
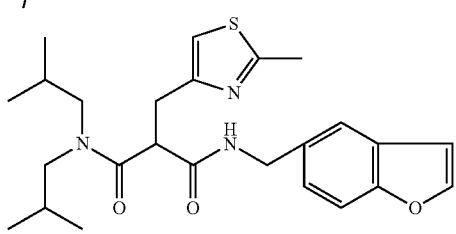
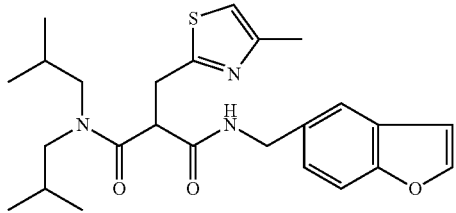
68
-continued
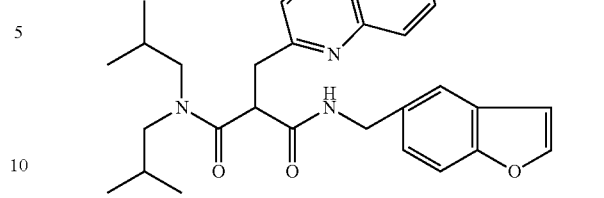
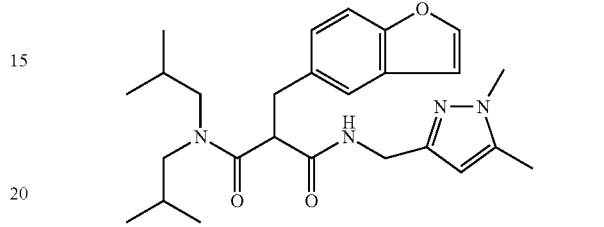
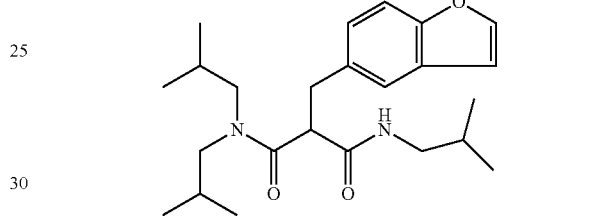
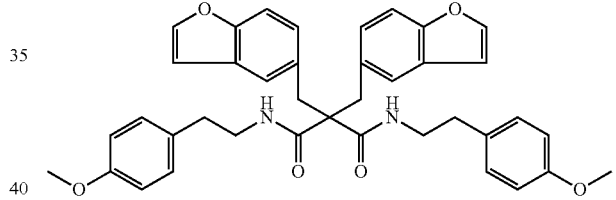
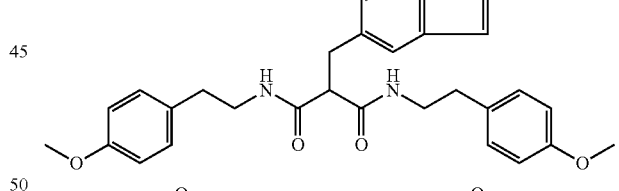
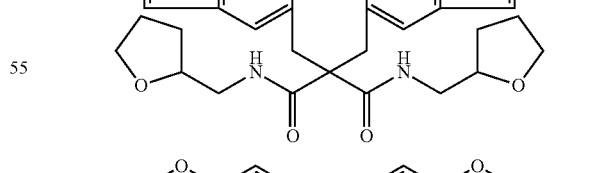
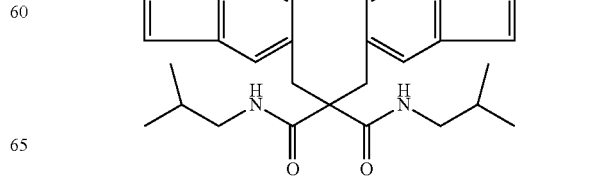

69
-continued
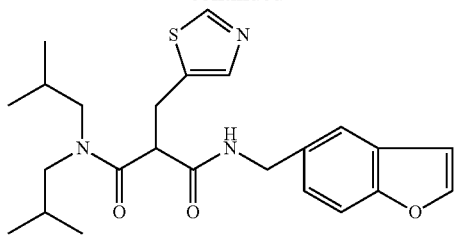
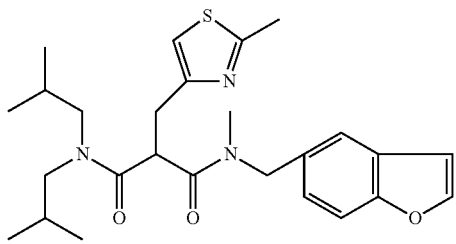
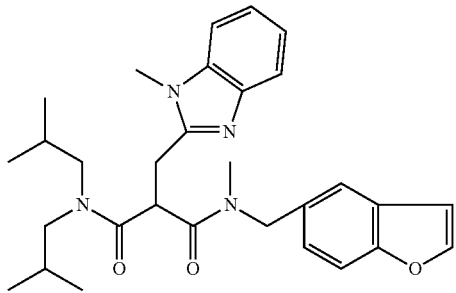
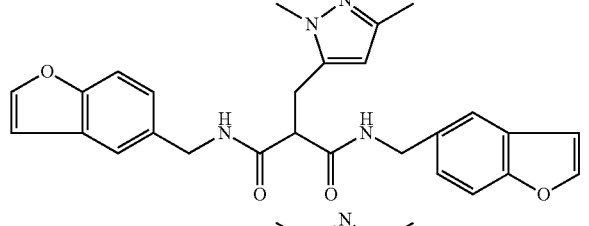
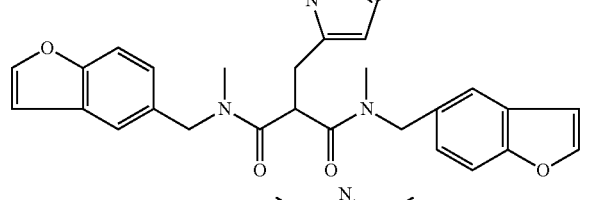
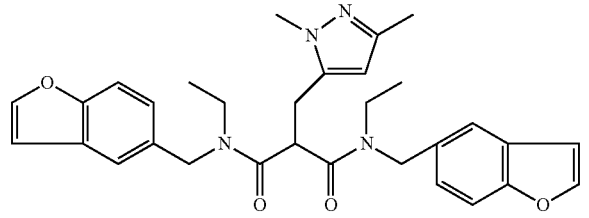
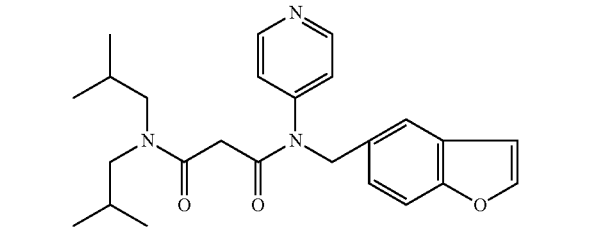
70
-continued
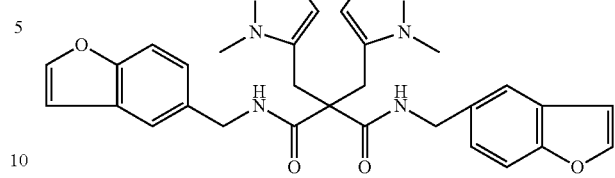
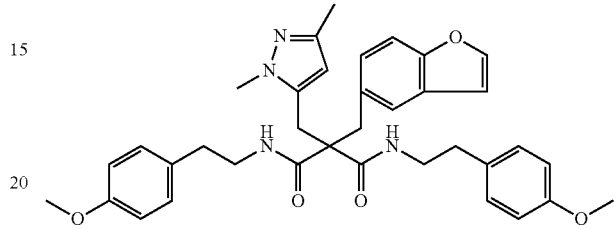
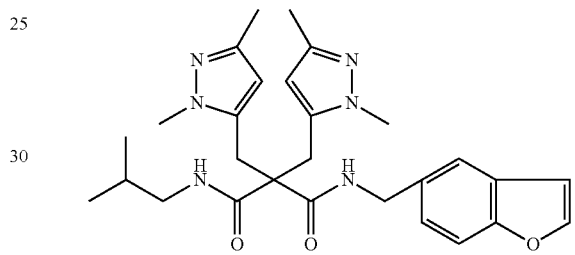
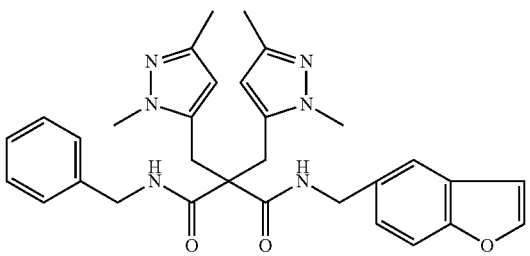
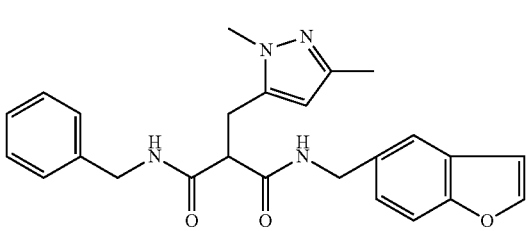
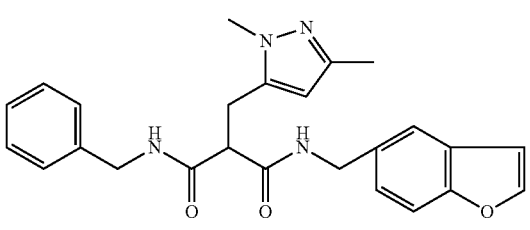
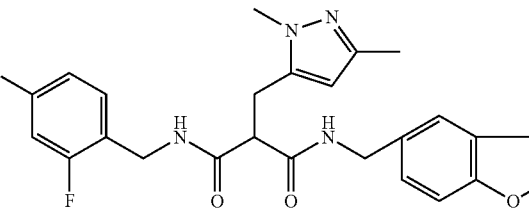

-continued
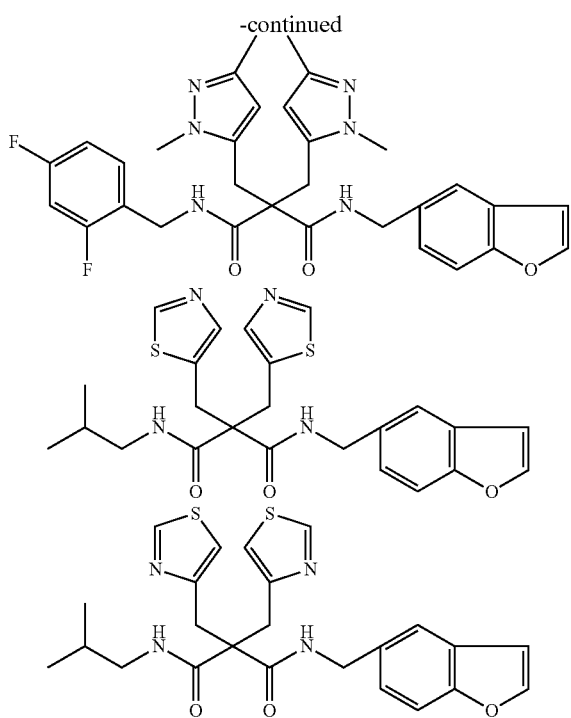
-continued
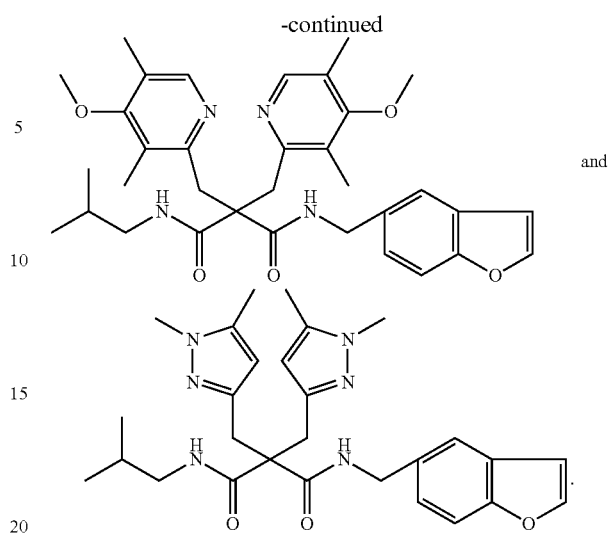
and
20. The method according to claim 1, wherein in is 1.
21. The method according to claim 1, wherein at least one of $R^1$, $R^2$, $R^3$, $R^4$, $R^5$, and $R^6$ is $CH_2$-benzofuranyl.
22. The method according to claim 21 wherein $R^5$ is —$CH_2$-benzofuranyl.
* * * * *